US011986198B2

(12) United States Patent
Behymer

(10) Patent No.: US 11,986,198 B2
(45) Date of Patent: May 21, 2024

(54) FORCEPS JAW ACTIVATION

(71) Applicant: GYRUS ACMI, INC., Southborough, MA (US)

(72) Inventor: Bruce Behymer, Grant, MN (US)

(73) Assignee: Gyrus ACMI, Inc., Westborough, MA (US)

(*) Notice: Subject to any disclaimer, the term of this patent is extended or adjusted under 35 U.S.C. 154(b) by 402 days.

(21) Appl. No.: 16/829,225

(22) Filed: Mar. 25, 2020

(65) Prior Publication Data
US 2020/0305956 A1    Oct. 1, 2020

Related U.S. Application Data

(60) Provisional application No. 62/994,220, filed on Mar. 24, 2020, provisional application No. 62/841,476, (Continued)

(51) Int. Cl.
A61B 17/28      (2006.01)
A61B 17/128     (2006.01)
(Continued)

(52) U.S. Cl.
CPC ........ *A61B 17/282* (2013.01); *A61B 17/1285* (2013.01); *A61B 17/2804* (2013.01); *A61B 17/2833* (2013.01); *A61B 17/285* (2013.01); *A61B 17/2909* (2013.01); *A61B 18/1445* (2013.01); *A61B 18/149* (2013.01); *A61B 90/03* (2016.02); *B23K 26/21* (2015.10); *A61B 2017/2845* (2013.01); *A61B 17/29* (2013.01); *A61B 2017/2901* (2013.01); *A61B 2017/2902* (2013.01); *A61B 2017/2903* (2013.01); *A61B 2017/2908* (2013.01); *A61B 2017/2912* (2013.01); *A61B 2017/2916* (2013.01); *A61B 2017/2917* (2013.01); *A61B 2017/2919* (2013.01); *A61B 2017/292* (2013.01); *A61B 2017/2925* (2013.01); *A61B 2017/2926* (2013.01); *A61B 2017/2933* (2013.01);
(Continued)

(58) Field of Classification Search
CPC ... A61B 17/282; A61B 17/1285; A61B 17/29; A61B 17/295; A61B 18/1445; A61B 2017/2902; A61B 2017/2919; A61B 2017/2926; A61B 2017/2933; A61B 2017/2947
See application file for complete search history.

(56) References Cited

U.S. PATENT DOCUMENTS 795,642 A      7/1905   Nelson
6,458,130 B1   10/2002  Frazier et al.
(Continued)

*Primary Examiner* — Brooke Labranche
(74) *Attorney, Agent, or Firm* — Schwegman Lundberg & Woessner, P.A.

(57) ABSTRACT

A forceps having an outer tube extending from a proximal portion to a distal portion and defining a longitudinal axis. A reciprocating inner tube can be located within the outer tube and extend along the longitudinal axis. A stationary jaw can be coupled to the distal portion of the outer tube and a moving jaw can be pivotably moveable relative to the stationary jaw. The moving jaw can be engaged with a portion of the reciprocating inner tube such that translation of the reciprocating inner tube pivots the moving jaw relative to the stationary jaw between an open and closed position.

23 Claims, 20 Drawing Sheets

Related U.S. Application Data filed on May 1, 2019, provisional application No. 62/826,532, filed on Mar. 29, 2019, provisional application No. 62/826,522, filed on Mar. 29, 2019.

(51) Int. Cl.
| | |
|---|---|
| *A61B 17/285* | (2006.01) |
| *A61B 17/29* | (2006.01) |
| *A61B 18/14* | (2006.01) |
| *A61B 90/00* | (2016.01) |
| *B23K 26/21* | (2014.01) |
| *A61B 17/295* | (2006.01) |
| *A61B 17/32* | (2006.01) |
| *A61B 18/00* | (2006.01) |

(52) U.S. Cl.
CPC .............. *A61B 2017/2936* (2013.01); *A61B 2017/2945* (2013.01); *A61B 2017/2946* (2013.01); *A61B 2017/2947* (2013.01); *A61B 2017/2948* (2013.01); *A61B 17/295* (2013.01); *A61B 2017/320052* (2013.01); *A61B 2017/320095* (2017.08); *A61B 2018/00148* (2013.01); *A61B 2018/00196* (2013.01); *A61B 2018/00202* (2013.01); *A61B 2018/00309* (2013.01); *A61B 2018/00345* (2013.01); *A61B 2018/00601* (2013.01); *A61B 2018/0063* (2013.01); *A61B 2018/00636* (2013.01); *A61B 2018/0091* (2013.01); *A61B 2018/00916* (2013.01); *A61B 2018/00946* (2013.01); *A61B 2018/00952* (2013.01); *A61B 2018/1412* (2013.01); *A61B 18/1442* (2013.01); *A61B 18/1447* (2013.01); *A61B 2018/1455* (2013.01); *A61B 2018/1457* (2013.01); *A61B 2090/034* (2016.02)

(56) References Cited

U.S. PATENT DOCUMENTS

| | | | |
|---|---|---|---|
| 7,131,971 | B2 | 11/2006 | Dycus et al. |
| 7,540,872 | B2 | 6/2009 | Schechter et al. |
| 9,498,281 | B2 | 11/2016 | Kendrick |
| 9,700,335 | B2 | 7/2017 | Reinauer et al. |
| 2007/0179499 | A1* | 8/2007 | Garrison ............ A61B 18/1445 606/171 |
| 2014/0025071 | A1 | 1/2014 | Sims et al. |
| 2014/0148807 | A1* | 5/2014 | Kendrick ............... A61B 17/29 606/208 |
| 2019/0083118 | A1* | 3/2019 | Hirai .................... A61B 17/29 |
| 2019/0175256 | A1 | 6/2019 | Butler |
| 2019/0298399 | A1 | 10/2019 | Boone et al. |

* cited by examiner

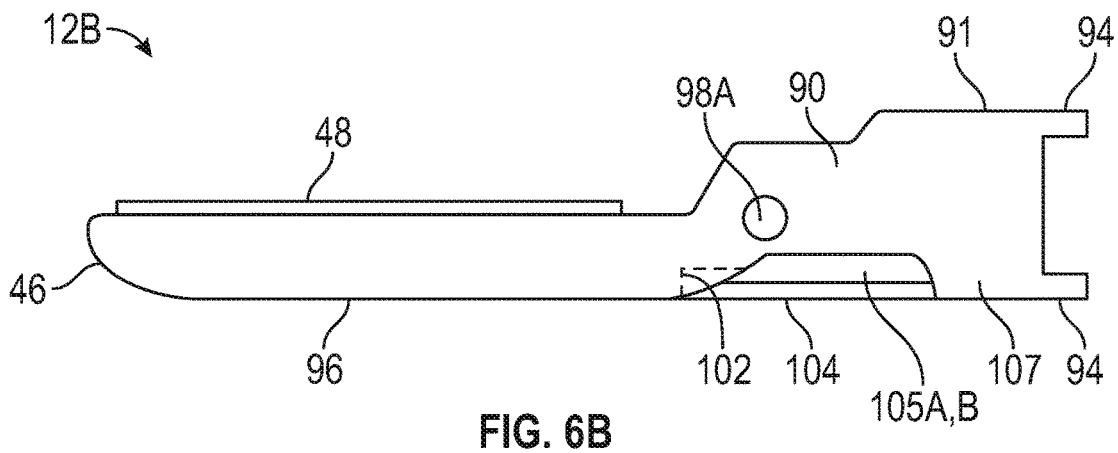
FIG. 6B
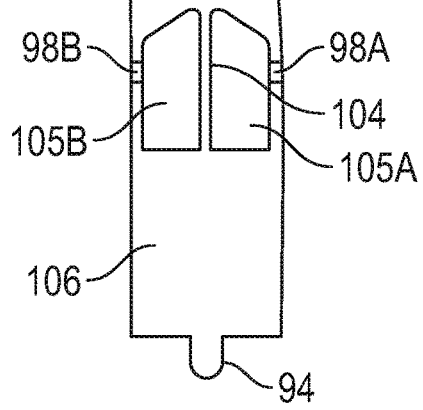
FIG. 6C
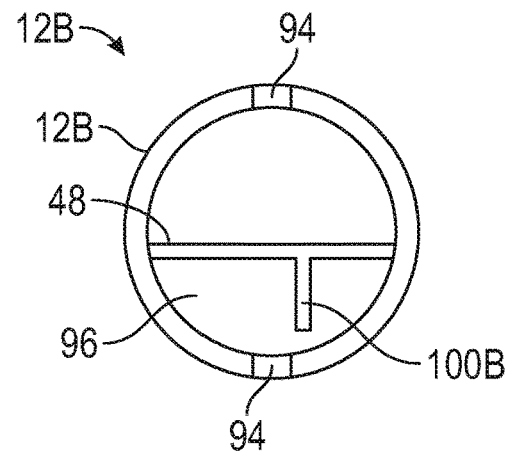
FIG. 6D
FIG. 6E

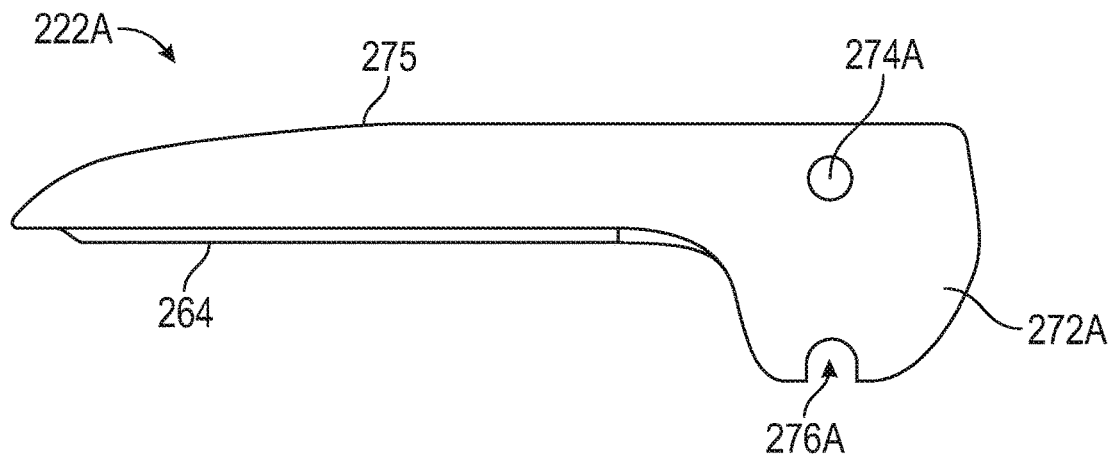
FIG. 13B
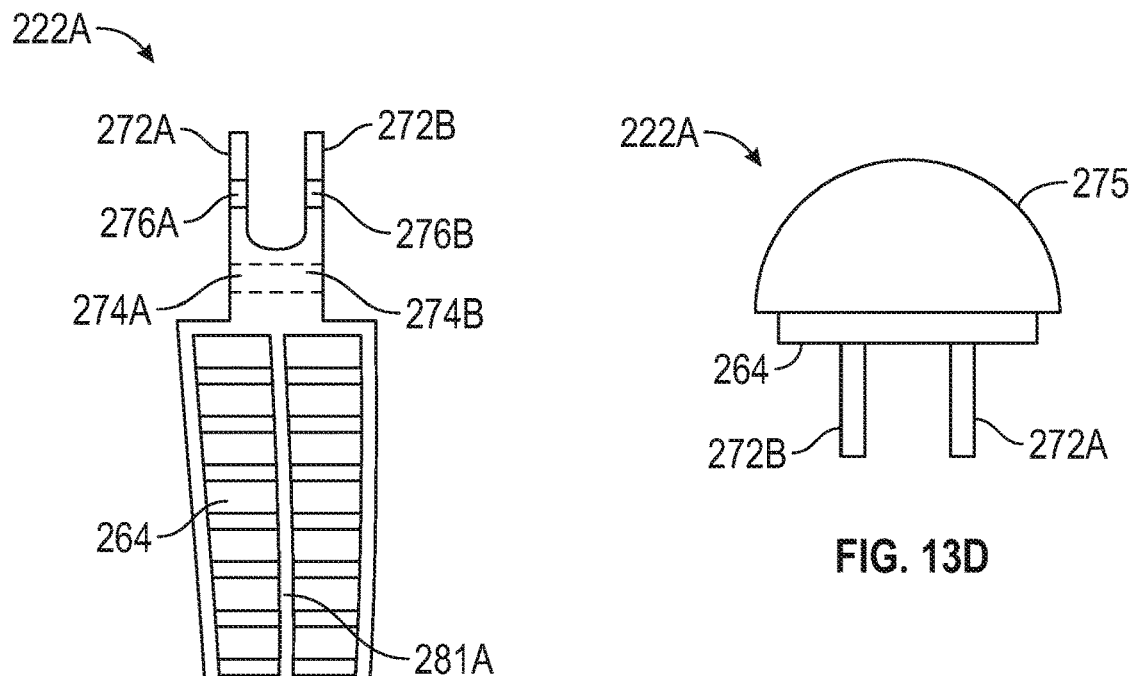
FIG. 13C
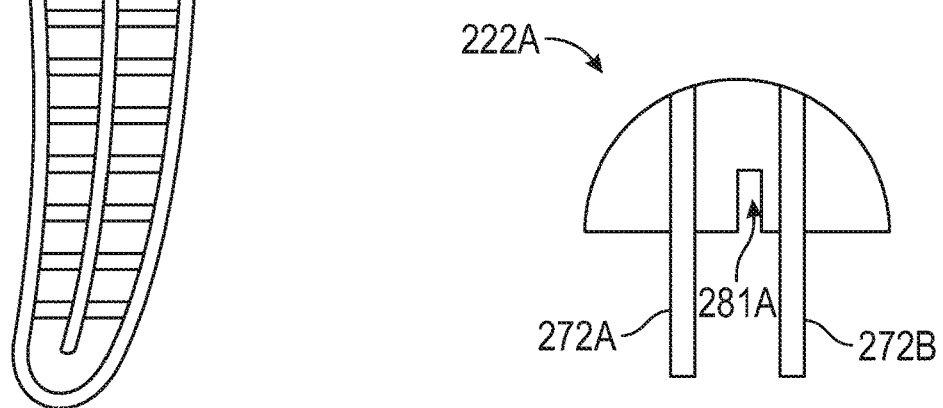
FIG. 13D
FIG. 13E

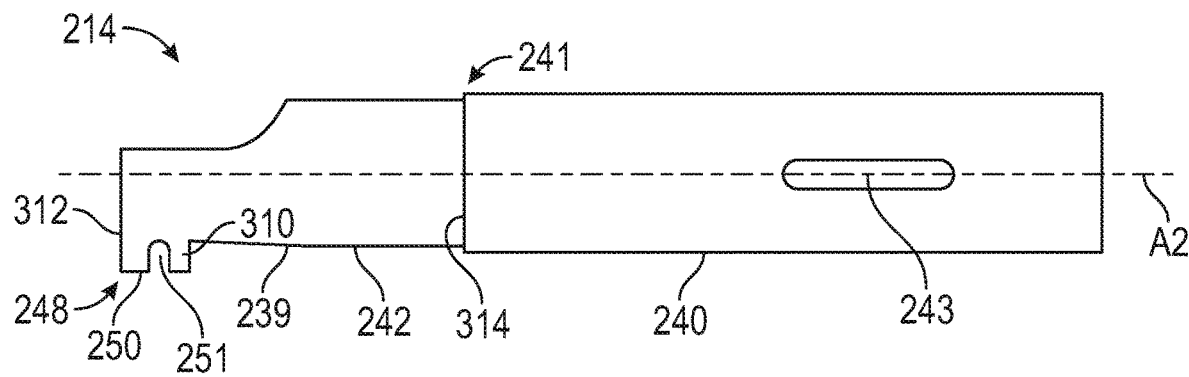
FIG. 16A
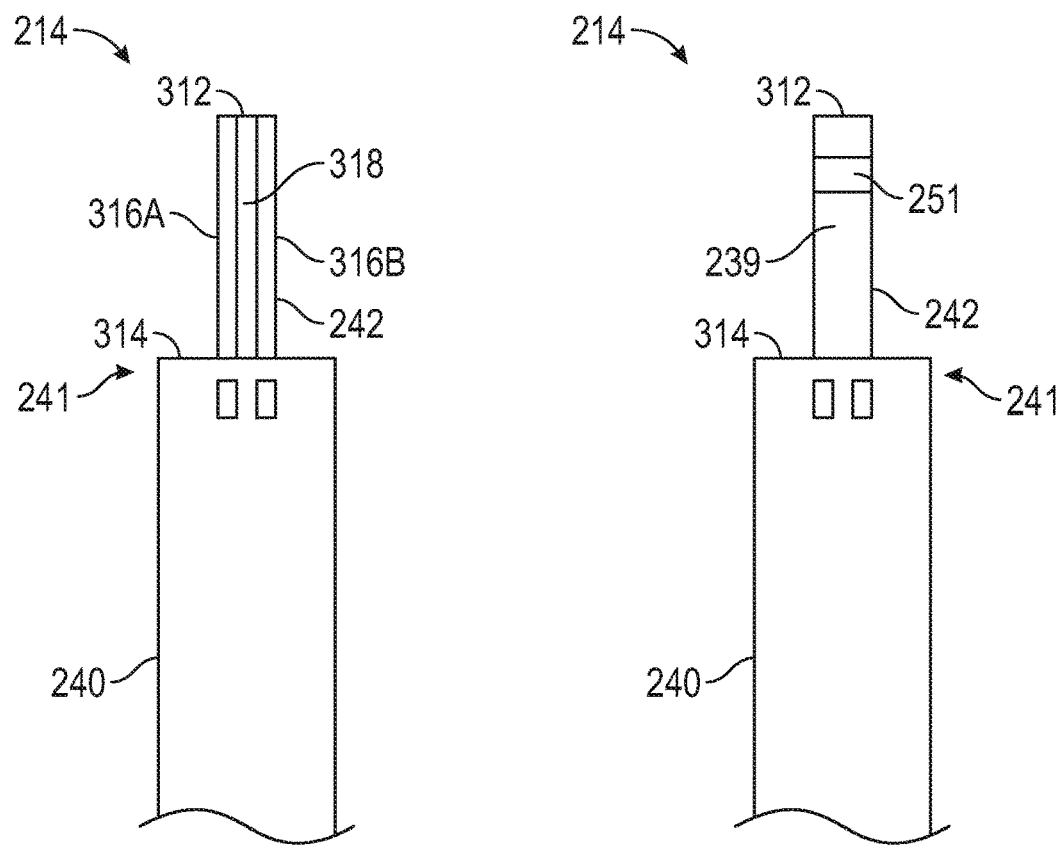
FIG. 16B
FIG. 16C
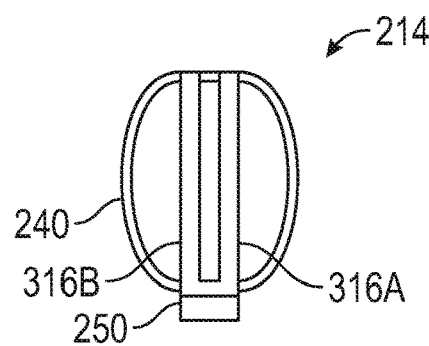
FIG. 16D

FORCEPS JAW ACTIVATION

PRIORITY CLAIM

This application claims priority to U.S. Ser. No. 62/826,532, filed on Mar. 29, 2019, entitled "BLADE ASSEMBLY FOR FORCEPS", the disclosure of which is incorporated by reference in its entirety. This application also claims priority to U.S. Ser. No. 62/826,522 filed on Mar. 29, 2019, entitled "SLIDER ASSEMBLY FOR. FORCEPS", the disclosure of which is incorporated by reference in its entirety. This application also claims priority to U.S. Ser. No. 62/841,476, filed on May 1, 2019, entitled "FORCEPS WITH CAMMING JAWS", the disclosure of which is incorporated by reference in its entirety. This application also claims priority to U.S. Ser. No. 62/994,220, filed on Mar. 24, 2020, entitled "FORCEPS DEVICES AND METHODS", the disclosure of which is incorporated by reference in its entirety.

TECHNICAL FIELD

This document pertains generally, but not by way of limitation, to surgical devices such as forceps, and more particularly, to a forceps device having an actuatable jaw that is configured to grasp, manipulate, and/or treat tissue.

BACKGROUND

This disclosure relates to surgical devices such as a forceps device. Forceps devices (hereinafter referred to simply as forceps), including but not limited to electrosurgical forceps, are often used for surgical procedures such as laparoscopic and open surgeries. The forceps can be used to manipulate, engage, grasp, or otherwise interact with anatomical features, such as a vessel or other tissue.

Forceps can include an end effector that is one or more of: rotatable, openable, closeable, extendable, retractable and capable of supplying an input such as electrosurgical energy or ultrasound. For example, jaws located at a distal end of the forceps can be actuated via elements at a handpiece of the forceps to cause the jaws to open and close and thereby engage a vessel or other tissue. Forceps may also include an extendable and retractable blade, or other end effector type device.

OVERVIEW

The present inventor has recognized, among other things, that problems to be solved with forceps include minimizing potential damage to surrounding tissues when actuating the jaw members of the end effector during medical procedures. Previous forceps generally include a drive member coupled to the moveable jaw member(s) via one or more cam pins operably coupled to corresponding cam slots disposed on the moveable jaw members(s). As is conventional, the cam slots are disposed on flanges of the jaw members. When transitioned from the closed position to the open position, the flanges can extend beyond the diameter of an outer tube of the forceps device. Extending beyond the diameter of the outer tube can cause problems by catching or damaging surrounding tissue. For example, once in a partially open or fully open position, the forceps generally will be manipulated until the jaws are in the desired position. The movement as the jaw members are in a partially or fully open position can cause the portion of the device extending beyond the diameter of the outer tube to come into contact and move against surrounding tissue. Depending on the movement and type of surrounding tissue, the contact and movement between the portion of the device and surrounding tissue can cause damage to the surrounding tissue. Therefore, the present inventors have recognized there is a need for improved forceps by reducing the amount or parts of the forceps that extend beyond the diameter of the outer tube when transitioning the moveable jaw members between the closed and open positions.

The present subject matter can provide solutions to these problems and other problems, such as by providing systems that transition the jaw members between closed and open positions while minimizing or preventing parts of the forceps extending beyond the diameter of the outer tube.

In an example, a surgical forceps can comprise an outer shaft extending from a proximal portion to a distal portion and defining a longitudinal axis, an inner shaft located within the outer shaft and extending along the longitudinal axis, the inner shaft including a projection at the distal portion of the inner shaft, a first jaw rigidly coupled to the distal portion of the outer shaft, and a second jaw pivotably moveable relative to the first jaw, the second jaw including a set of flanges located at a proximal portion of the second jaw, each flange of the set of flanges engagable with the projection of the inner tube, the inner shaft translatable within the outer shaft to pivot the second jaw relative to the first jaw and the outer shaft between open and closed positions.

In another example, a surgical forceps can comprise an outer shaft extending from a proximal portion to a distal portion and defining a longitudinal axis, a drive bar located within the outer tube and extending along the longitudinal axis, the drive bar including: a drive bar shaft extending from a proximal portion to a distal portion, and a drive bar strut coupled to the distal portion of the drive bar shaft, a first jaw rigidly coupled to the distal portion of the outer shaft, the first jaw including a first set of flanges, and a second jaw pivotably moveable relative to the first jaw, the second jaw including a second set of flanges located at a proximal portion of the second jaw, each flange of the second set of flanges coupled to the drive bar strut of the drive bar, the drive bar translatable within the outer shaft to pivot the second jaw relative to the first jaw and the outer shaft between open and closed positions.

In an additional example, a surgical forceps can comprise an outer shaft extending from a proximal portion to a distal portion and defining a longitudinal axis, a drive bar located within the outer shaft and extending along the longitudinal axis, the drive bar including: a drive bar shaft extending from a proximal portion to a distal portion, and a drive bar strut coupled to the distal portion of the drive bar shaft, a first jaw rigidly coupled to the distal portion of the outer tube, the first jaw having a first set of flanges located at a proximal portion of the first jaw, a second jaw pivotably moveable relative to the first jaw and the outer tube, the second jaw including a second set of flanges located at a proximal portion of the second jaw, a pivot pin securable to the second set of flanges, wherein the pivot pin is offset from the longitudinal axis, and a drive pin securable to the drive bar strut and the second set of flanges, wherein the drive pin is offset from the longitudinal axis, the drive bar translatable within the outer shaft to drive the drive pin in a first direction along the outer shaft to pivot the second jaw, about the pivot pin, between a closed position and an open position.

The features described herein can be used with other devices besides forceps, such as medical devices (e.g., instruments) for performing treatment, diagnosis and imaging. The devices and methods can be employed in a variety of medical areas, including, but not limited to, general surgery, gynecology, urology, respiratory, cardiovascular, or any other suitable area.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

FIG. 6B illustrates a side-view of the bottom jaw shown in FIG. 6A.

FIG. 6C illustrates a bottom-up view of the bottom jaw shown in FIGS. 6A-B.

FIG. 6D illustrates a distal view of the bottom jaw shown in FIG. 6A-C.

FIG. 6E illustrates a proximal view of the bottom jaw shown in FIGS. 6A-6D.

FIG. 13B illustrates a side-view of the top jaw shown in FIG. 13A.

FIG. 13C illustrates a bottom-up view of the top jaw shown in FIGS. 13A-B.

FIG. 13D illustrates a distal view of the top jaw shown in FIG. 13A-C.

FIG. 13E illustrates a proximal view of the top jaw shown in FIGS. 13A-4D.

FIG. 16A illustrates side-view of the inner shaft, in accordance with at least one example of this disclosure.

FIG. 16B illustrates top-down view of the inner shaft shown in FIG. 16A.

FIG. 16C illustrates a bottom-up view of the inner shaft shown in FIGS. 16A and 16B.

FIG. 16D illustrates a distal view of the inner shaft shown in FIGS. 16A-C.

Figure 1:
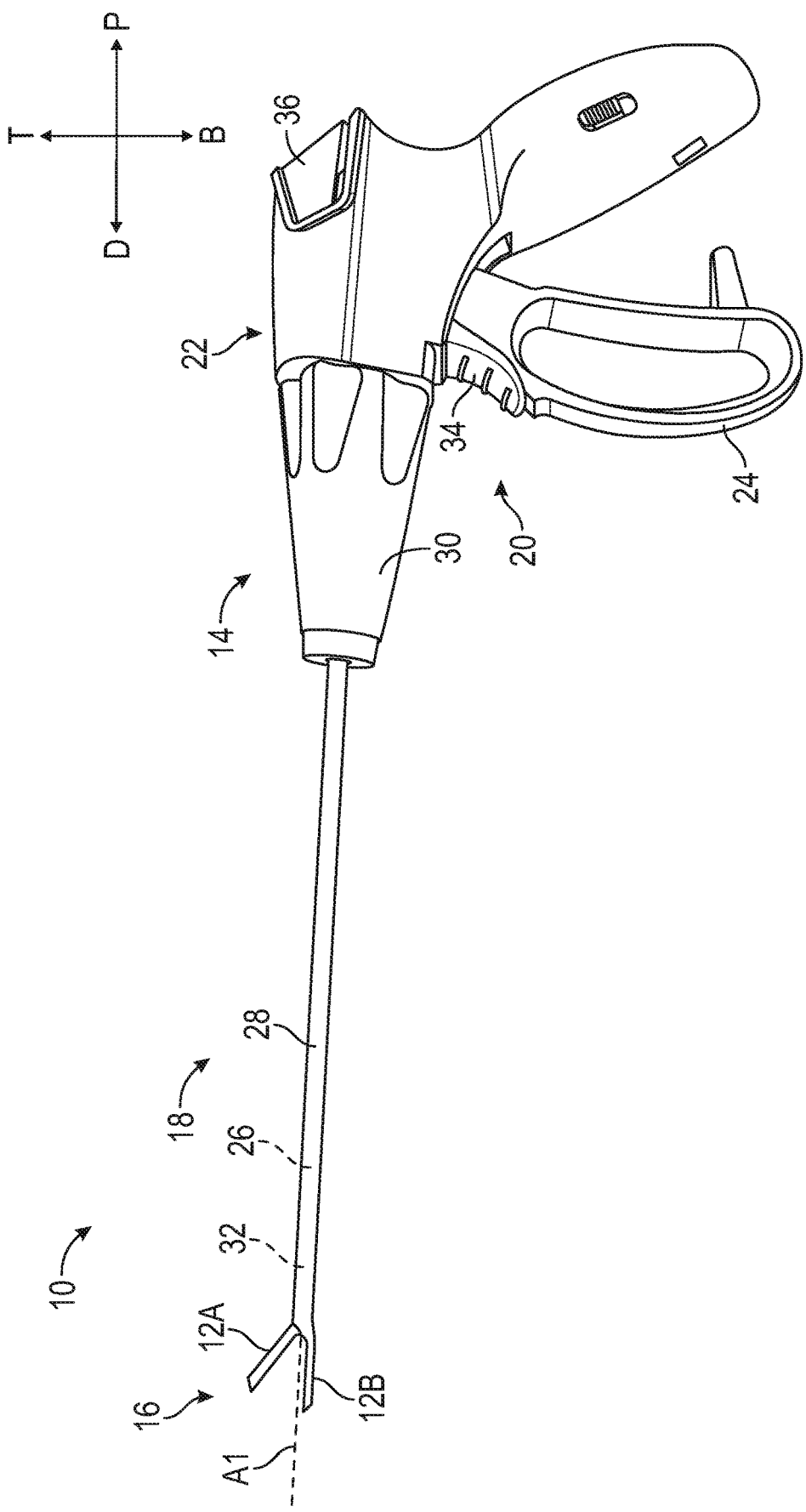
FIG. 1 illustrates a side view of a forceps showing jaws in an open position, in accordance with at least one example of this disclosure.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

A medical device including a handpiece that operates an end effector allows a surgeon to control the end effector of the device to actuate one or more functions of the end effector. Actuation of the end effector can be facilitated by one or more actuation systems of the handpiece that can retract, extend or rotate one or more shafts to control the actions of the end effector.

This disclosure is generally related to medical devices, such as surgical instruments. Although the present application is described with reference to a forceps, other end effectors can be used with and operated by the handpiece described herein. In addition, other handpieces can be connected to and can control the end effectors described herein. This disclosure includes examples of handpieces including one or more actuation systems, examples of end effectors, and examples where the disclosed actuation systems and end effectors can be used together in a medical device.

The forceps can include a medical forceps, a cutting forceps, an electrosurgical forceps, or any other type of forceps. The forceps can include an end effector that is controlled by a handpiece including an actuation system to be one or more of: rotatable, openable, closeable, extendable, and capable of supplying electrosurgical energy or ultrasound. For example, jaws located at a distal end of the forceps can be actuated via one or more actuators at a handpiece of the forceps to cause the jaws to open, close and rotate to engage a vessel or other tissue. Forceps may also include an extendable and retractable blade, such as blades that can be extended distally in between a pair of jaws to separate a first tissue from a second tissue.

FIG. 1 illustrates a side view of a forceps 10 with jaws 12 (including a top jaw 12A and bottom jaw 12B; collectively referred to as jaws 12) in an open position. Directional descriptors such as proximal and distal are used within their ordinary meaning in the art. The proximal direction P and distal direction D, as well as top T and bottom B, are indicated on the axes provided in FIG. 1. The forceps can include a handpiece 14, one or more actuators 20, an outer shaft 28 (or outer tube), an inner shaft 26 (or inner tube or drive shaft), and an end effector 16.

The forceps 10 can include the handpiece 14 at a proximal end and the end effector 16 at a distal end. An intermediate portion 18 can extend between the handpiece 14 and the end effector 16 to operably couple the handpiece 14 to the end effector 16. Various movements of the end effector 16 can be controlled by one or more actuation systems 20 of the handpiece 14. In the illustrative example, the end effector 16 can include the jaws 12 that are capable of moving between an open position and a closed position. The end effector 16 can be rotated along a longitudinal axis A1 of the forceps 10. The end effector 16 can include a cutting blade and an electrode for applying electrosurgical energy.

As broadly shown in FIG. 1, the forceps 10 can include the top jaw 12A and the bottom jaw 12B), a housing 22, a lever 24, the inner shaft 26, the outer shaft 28, a rotational actuator 30, a blade assembly 32 or blade 32 (including a blade shaft 32A and a cutting blade 32B of FIG. 2), a trigger 34 and an activation button 36. In this example, the end effector 16, or a portion of the end effector 16 can be one or more of: opened, closed, rotated, extended, retracted, and electrosurgical energized.

Figure 8A:
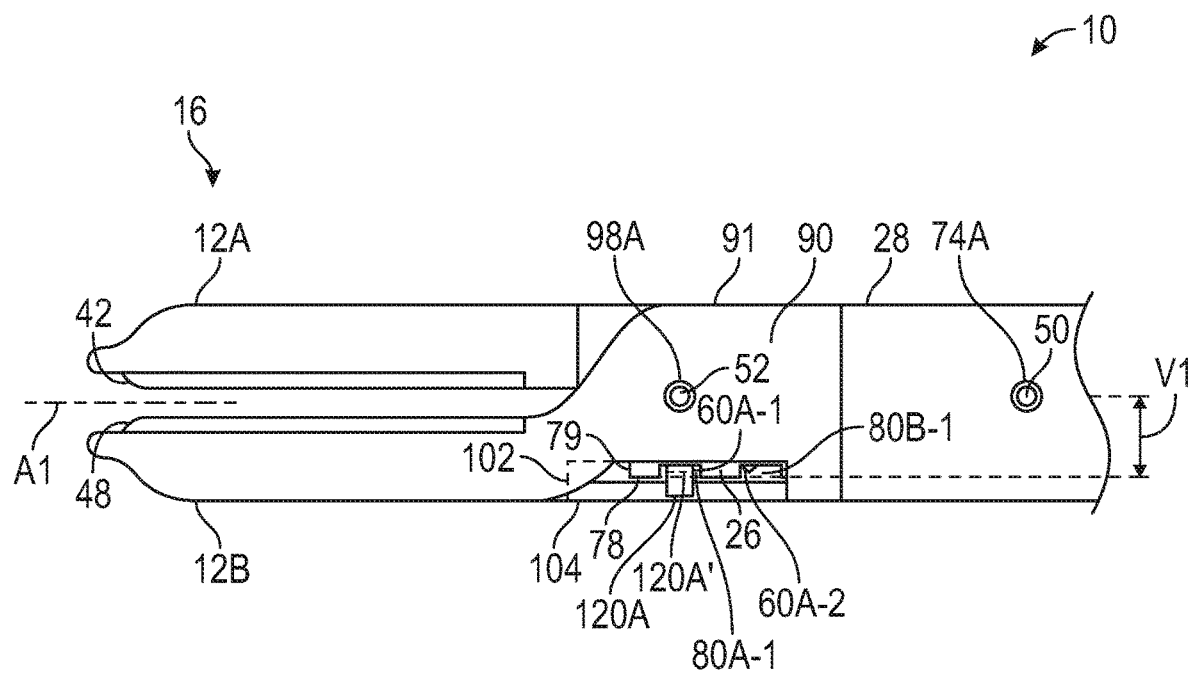
FIG. 8A illustrates a side-view of the end effector of the forceps showing the jaws in a closed position, in accordance with at least one example of this disclosure.

To operate the end effector 16, the user can displace the lever 24 proximally to drive the jaws 12 from the open position (FIG. 1) to the closed position (FIG. 8A). In the example of forceps 10, moving the jaws 12 from the open position to the closed position allows a user to clamp down on and compress a tissue. The handpiece 14 can also allow a user to rotate the end effector 16. For example, rotating rotational actuator 30 causes the end effector 16 to rotate by rotating both the inner shaft 26 and the outer shaft 28 together.

In some examples, with the tissue compressed, a user can depress the activation button 36 to cause an electrosurgical energy to be delivered to the end effector 16, such as to an electrode. Application of electrosurgical energy can be used to treat the tissue such as seal or otherwise affect the tissue being clamped. In some examples, the electrosurgical energy can cause tissue to be sealed, ablated, and/or coagulated. Example electrodes are described herein, but electrosurgical energy can be applied to any suitable electrode.

Figure 2:
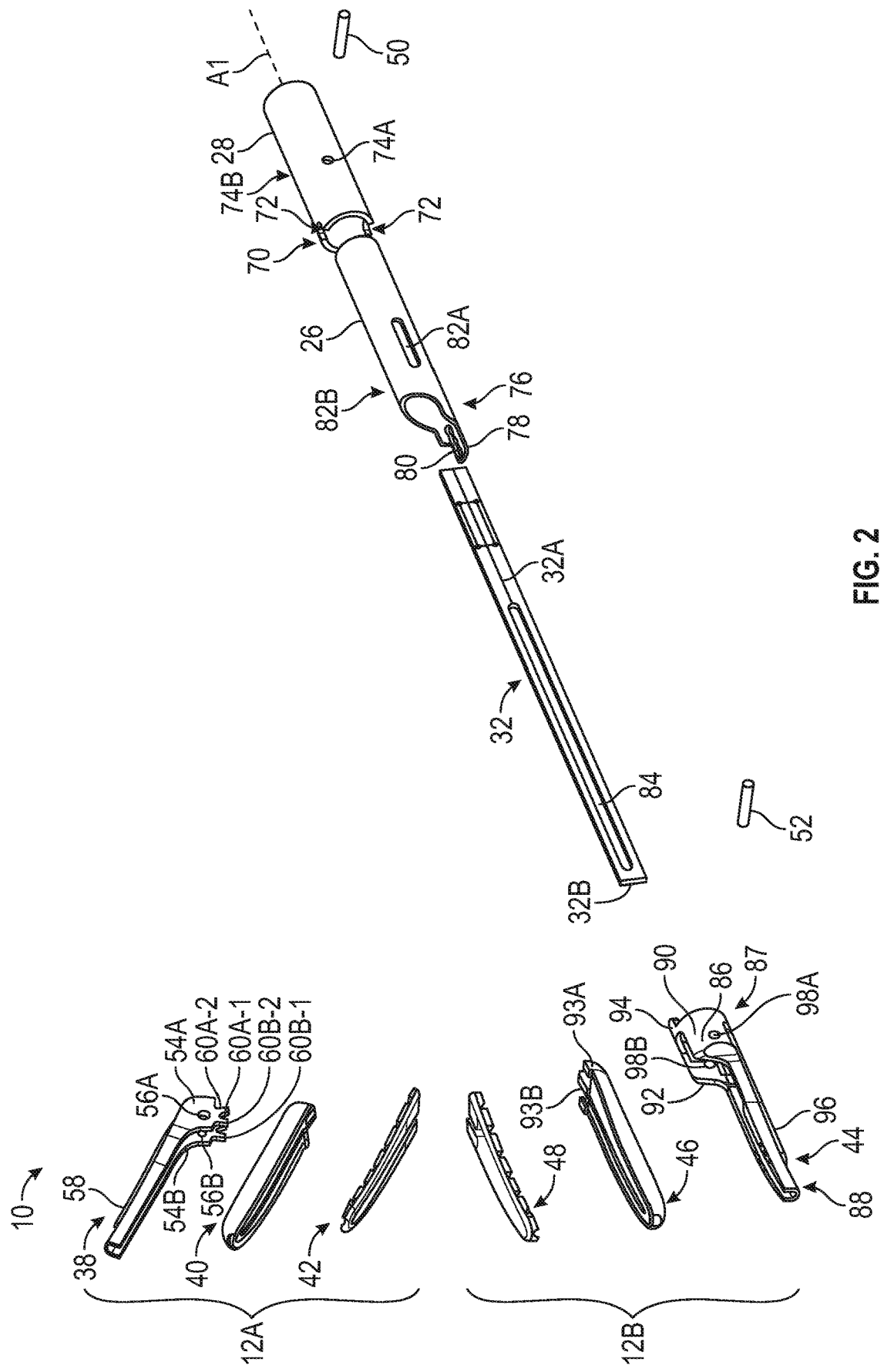
FIG. 2 illustrates an expanded view of a portion of the forceps, in accordance with at least one example of this disclosure.

In some examples, the forceps 10 can be used to cut the tissue via the blade 32. For example, the handpiece 14 can enable a user to extend and retract the blade 32 including a cutting blade 32A attached to a distal end of the blade shaft 32B (FIG. 2). The cutting blade 32A can be extended by displacing the trigger 34 proximally. The cutting blade 32A can be retracted by allowing the trigger 34 to return distally to a default position. The default position of the trigger 34 is shown in FIG. 1. In some examples, the handpiece 14 can include features that inhibit the blade 32A from being extended until the jaws 12 are at least partially closed, or fully closed.

The forceps 10 can be used to perform a treatment on a patient, such as a surgical procedure. In an example, a distal portion of the forceps 10, including the jaws 12, can be inserted into a body of a patient, such as through an incision or another anatomical feature of the patient's body, or down the length of a surgical access port, which may include a cannula. While a proximal portion of the forceps 10, including the housing 22 remains outside the incision, another anatomical feature of the body, or the surgical access port. Actuation of the lever 24 causes the jaws 12 to clamp onto a tissue. The rotational actuator 30 can be rotated via a user input to rotate the jaws 12 for maneuvering the jaws 12 at any time during the procedure. Activation button 36 can be actuated to provide electrical energy to jaws 12 to cauterize or seal the tissue within the closed jaws 12. Trigger 34 can be moved to translate the blade 32 distally in order to cut the tissue within the jaws 12.

The components of the forceps 10 can each be comprised of materials such as one or more of metals, plastics, foams, elastomers, ceramics, composites, combinations thereof, or the like. Materials of some components of the forceps are discussed below in further detail.

FIG. 2 illustrates an expanded view of a portion of the forceps 10. The forceps 10 can include the top jaw 12A, the bottom jaw 129, the inner shaft 26, the outer shaft 28, the blade 32, a guide (or proximal pin) 50, and a pivot pin 52. As discussed herein, the bottom jaw 12B can be stationary and is rigidly coupled to a distal portion 70 of the outer shaft 28. The top jaw 12A can be moveable and is pivotably coupled to the bottom jaw 12B. The top jaw 12A can be engaged with a portion of the inner shaft 26 such that translation of the inner shaft 26 along the longitudinal axis A1 can pivot the top jaw 12A relative to the bottom jaw 12B. That is, the linear movement of the inner shaft 26 can be translated into rotational motion to rotate the top jaw 12A about the pivot pin 52 from a closed position to an open position.

Each of the inner shaft 26 and the outer shaft 28 can be a rigid or semi-rigid and include an elongate body having a geometric shape of a cylinder, where the shape of the inner shaft 26 matches the shape of the outer shaft 28. In some examples, the inner shaft 26 and the outer shaft 28 can have other shapes such as an oval prism, a rectangular prism, a hexagonal prism, an octagonal prism, or the like. In some examples, a portion of the inner shaft 26 and a corresponding portion of the outer shaft 28 can have a non-rotational shape. That is, while the inner shaft 26 can be moved relative to the outer shaft 28 along the longitudinal axis A1, the inner shaft 26 and the outer shaft 28 are rotationally coupled or rotationally locked. Therefore, rotational motion applied to the inner shaft 26 will rotate the outer shaft 28 and rotational motion applied to the outer shaft 28 will rotate the inner shaft 26. In some examples, the shape of the inner shaft 26 can be different from the shape of the outer shaft 28.

The outer shaft 28 can extend from a proximal portion to a distal portion 70 along the longitudinal axis A1. Similarly, the inner shaft 26 can extend from a proximal portion to a distal portion 76 along the longitudinal axis. In an example, the longitudinal axis A1 can be a central axis of one or more of the inner shaft 26 and the outer shaft 28. The inner shaft 26 can include an axial bore extending along the longitudinal axis A1. The outer shaft 28 can also include an axial bore extending along the longitudinal axis A1. The inner shaft 26 can have an outer dimension (such as an outer diameter) smaller than an inner diameter of the outer shaft 28 such that the inner shaft 26 can be positioned within the outer shaft 28 and can be translatable therein along the longitudinal axis A1.

As discussed herein, the outer shaft 28 can be coupled to the bottom jaw 12B. In an example, the distal portion 70 of the outer shaft 28 can include one or more recesses 72 that can receive a corresponding projection 94 on the bottom jaw 12B. While a recess and projection are shown, any mechanism to rotationally lock and linearly lock the outer shaft 28 to the bottom jaw 12B is contemplated. In one example, a portion of the bottom jaw 12B, such as the jaw body 90, can be secured to the outer shaft 28, e.g., by welding.

The inner shaft 26 can include a projection 78 extending along the distal portion 76 of the inner shaft 26. In an example, the projection 78 can include at least one set of openings 80 configured to receive and engage with the projections 60A-1, 60A-2, 60B-1, and 60B-1 (collectively referred to as projections 60).

The blade 32 can be an elongate cutting member including the blade shaft 32B and have one or more sharpened edges (cutting blade 32B) configured to cut or resect tissue or other items. The blade 32 can be located within the outer shaft 28 (and within the inner shaft 26) and can extend along (and optionally parallel with) the longitudinal axis A1. The blade 32 can be translatable with respect to the inner shaft 26 and the outer shaft 28 to extend between (or into) the top jaw 12A and the bottom jaw 12B. In some examples, the blade 32 can extend axially through the inner shaft 26 offset from the longitudinally axis A1.

The guide 50 and the pivot pin 52 can each be a rigid or semi-rigid pin, such as a cylindrical pin. The guide 50 and the pivot pin 52 can have other shapes in other examples, such as rectangular, square, oval, or the like. In some examples, each pin can be the same size (e.g. diameter and length) to simplify manufacturing and reduce cost. Each pin can have a smooth surface to help reduce surface friction between the pins and components of the forceps 10, such as between the pivot pin 50 and the jaws 12A, 12B and between the guide 50 and the outer shaft 28. In some examples, each of the guide 50 the pivot pin 52 can be other components such as one or more projections, bosses, arms, or the like.

As seen in FIG. 2, the outer shaft 28 can include includes openings 74A and 74B (only one opening 74A is visible in FIG. 2; collectively referred to as openings 74) on opposite sides of the outer shaft 28 to receive the guide 50. The guide 50 can be secured to the outer shaft 28 such as by insertion into openings 74A, 74B. In an example, the guide 50 can be coupled to the outer shaft 28 by, e.g., by welding.

The inner shaft 26 can include a pair of axial tracks 82A and 82B (only one axial track 82A is visible in FIG. 2; collectively referred to as axial tracks 82) located on opposite sides of the inner tube 26. The pair of axial tracks 82 arranged to receive the guide 50 therein. As discussed herein, the inner tube 26 is moveable relative to the guide 50 as the inner tube 26 translates relative to the outer shaft 28. The axial tracks 82 can each be axial slots extending laterally through walls of the inner shaft 26. In other example, the axial tracks 82 can be channels, grooves, recesses, or other guides configured to receive a guiding member. In some examples, the axial tracks 82 do not extend entirely through the inner shaft 2026.

The axial tracks 82 can be sized and shaped to receive the guide 50 therein and can be sized and shaped for the guide 50 to translate within the axial tracks 82 between a proximal edge and a distal edge of the axial tracks 82. Distal translation of the inner shaft 26 relative to the outer shaft 28 can be limited, for example, by contact between the guide 50 and the proximal edges of the respective axial tracks 82. However, other configurations for limiting the distal translation of the inner shaft 26 is contemplated. Additionally, the guide 50 received within axial tracks 82 can secure the inner shaft 26 from vertical displacement and/or rotational displacement with respect to the outer shaft 28.

The blade 32 can include an axial opening 84 extending along the blade shaft 32A. The axial opening 84 is sized and shaped to receive both the guide 50 and the pivot pin 52. As the blade 32 translates relative to the outer shaft 28 and the inner shaft 26, the axial opening 84 receives and moves relative to the pivot pin 52 and the guide 50. The axial opening 84 extends from a distal edge to a proximal edge. Distal translation of the blade 32 can be limited, for example, by contact between the guide 50 and the proximal edge of the axial opening 84. However, other configurations for limiting the distal translation of the blade 32 are contemplated.

Figure 3:
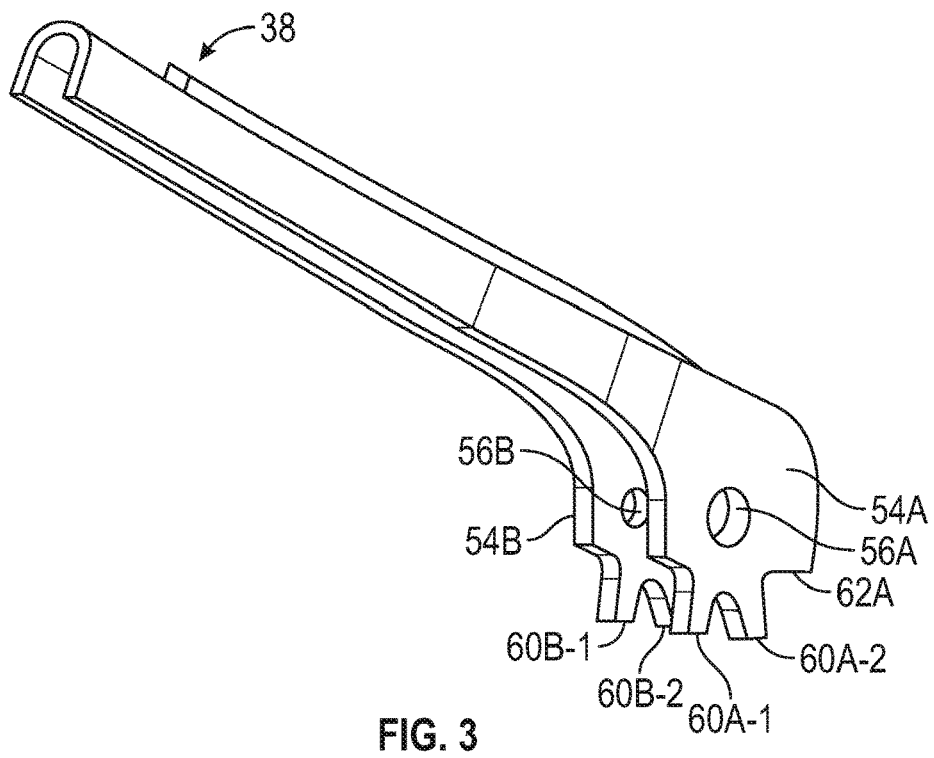
FIG. 3 illustrates a perspective view of a jaw body of the top jaw, in accordance with least one example of this disclosure.
Figure 4A:
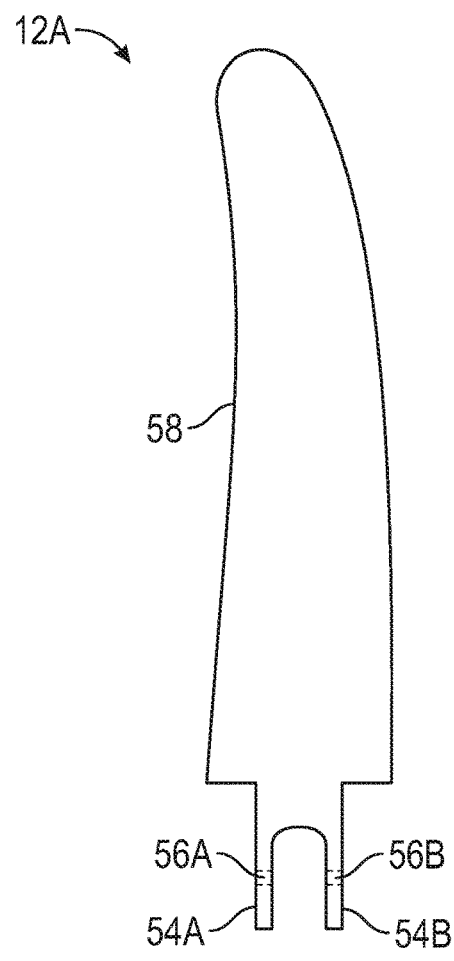
FIG. 4A illustrates a top-down view of the top jaw, in accordance with at least one example of this disclosure.
Figure 4B:
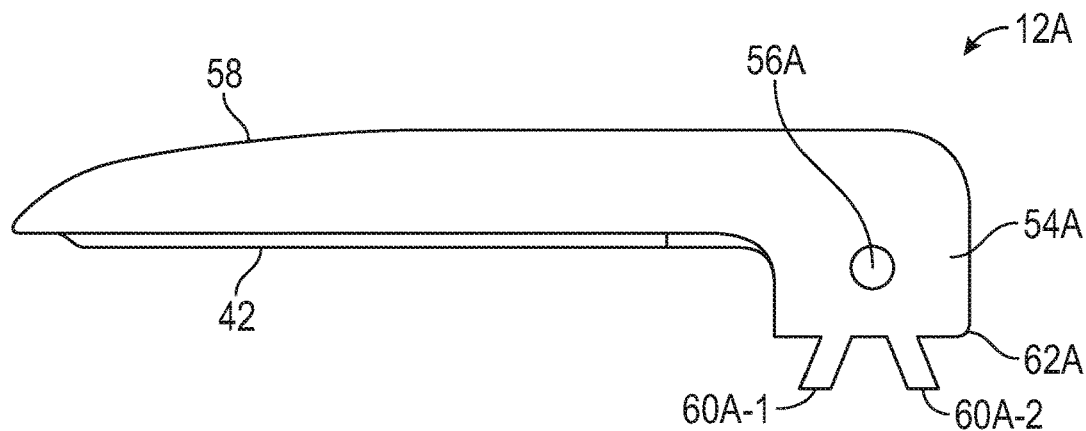
FIG. 4B illustrates a side-view of the top jaw shown in FIG. 4A.
Figure 4C:
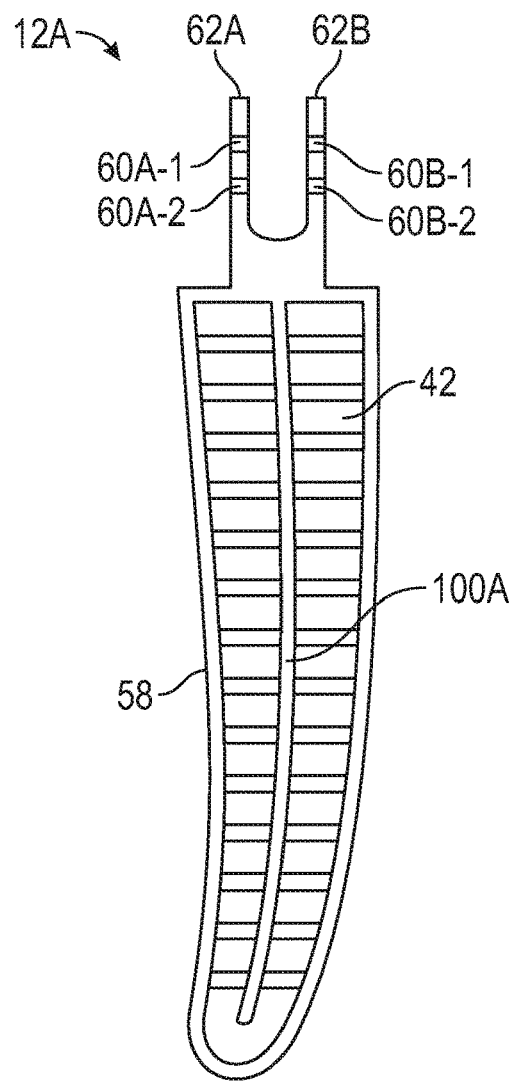
FIG. 4C illustrates a bottom-up view of the top jaw shown in FIGS. 4A-B.
Figure 4D:
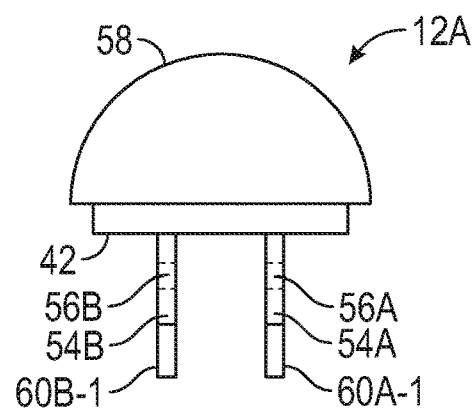
FIG. 4D illustrates a distal view of the top jaw shown in FIG. 4A-C.
Figure 4E:
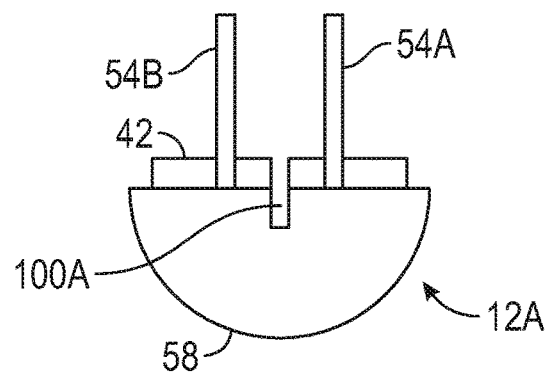
FIG. 4E illustrates a proximal view of the top jaw shown in FIGS. 4A-4D.
Figure 5:
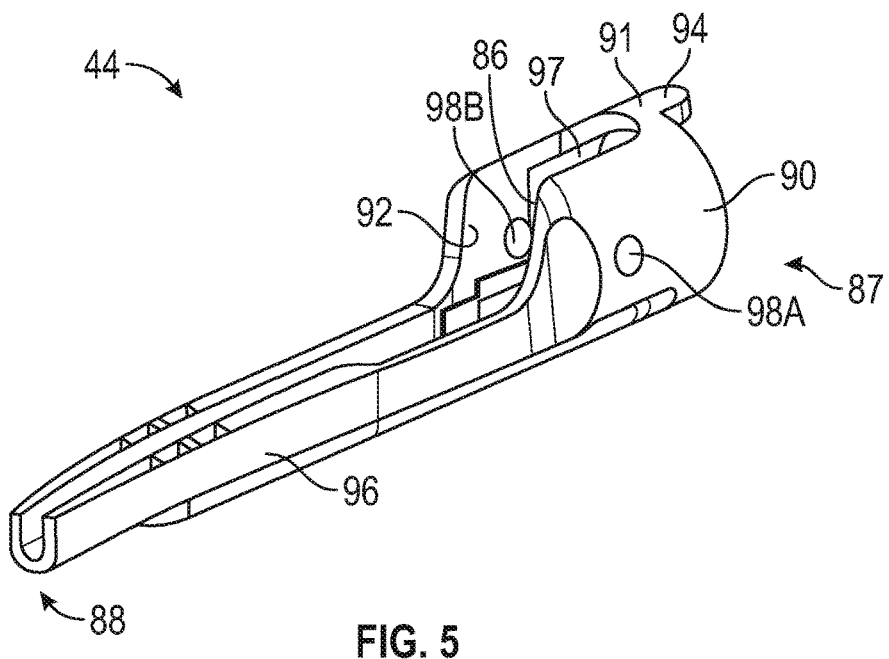
FIG. 5 illustrates a perspective view of a jaw body of the bottom jaw, in accordance with least one example of this disclosure.
Figure 6A:
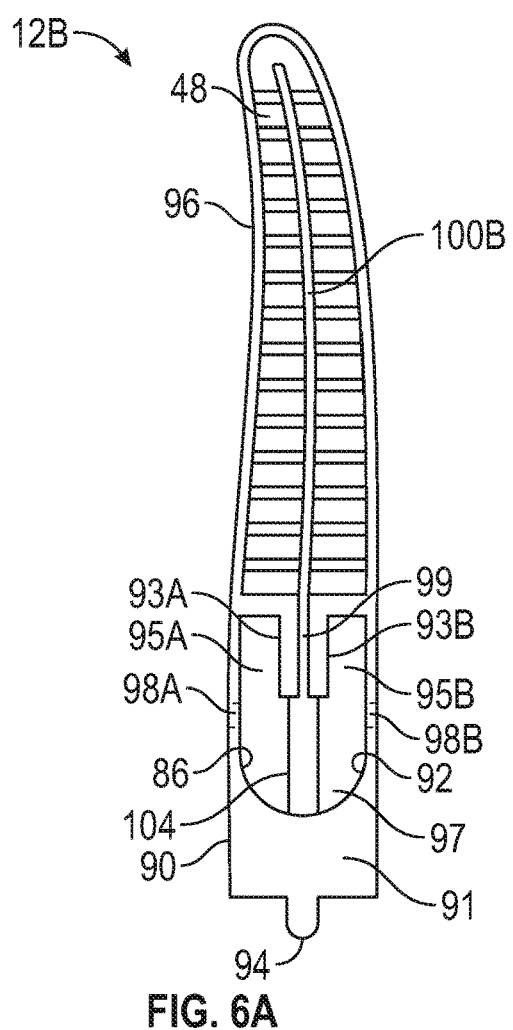
FIG. 6A illustrates a top-down view of the bottom jaw, in accordance with at least one example of this disclosure.

FIGS. 3-4E illustrate views of the top jaw 12A and FIGS. 5-6D illustrate views of the bottom jaw 12B. In particular, FIG. 3 illustrates a perspective view of a jaw body 38 of the forceps 10, FIG. 4A illustrates a top down view of top jaw 12A, FIG. 4B illustrates a side-view of the top jaw 12A, FIG. 4C illustrates a bottom-up view of the top jaw 12A, FIG. 4D illustrates a front view or distal view of the top jaw 12A, and FIG. 4E illustrates a back-end view or proximal view of the top jaw 12A. FIG. 5 illustrates a perspective view of a jaw body 48 of the forceps 10, FIG. 6A illustrates a top down view of the bottom jaw 12B (the bottom jaw member), FIG. 6B illustrates a side-view of the bottom jaw 12B, FIG. 6C illustrates a bottom-up view of the bottom jaw 129, FIG. 6D illustrates a front view or distal view of the bottom jaw 12B, and FIG. 6E illustrates a back-end view or proximal view of the bottom jaw 12B.

The forceps 10 will now be discussed referencing FIGS. 1-6E. The end effector 16 can include the top jaw 12A and the bottom jaw 12B (collectively referred to herein as jaws 12). The top jaw 12A can include a top jaw body 38 (or jaw body 38), a top insulating portion 40, and a top grip plate 42. The bottom jaw 12B can include a bottom jaw body 44 (or jaw body 44), a bottom insulating portion 46, and a bottom grip plate 48. The combination of the jaw body 38, the top insulating portion 40, and the top grip plate 42 form the top jaw 12A. Similarly, the combination of the jaw body 44, the bottom insulating portion 46, and the bottom grip plate 42 form the bottom jaw 12B. While illustrated as separate components, one or more of the jaw body, insulating portions, and grip plates of each respective jaw can be formed as one integral component.

The grip plates 42 and 48 of the jaws 12 can each be a rigid or semi-rigid member configured to engage tissue and/or the opposing jaw to grasp tissue, such as during an electrosurgical procedure. One or more of the grip plates 42, 48 can include one or more of serrations, projections, ridges, or the like configured to increase engagement pressure and friction between the grip plates 42, 48 and tissue. The jaws 12 can each include an electrode configured to deliver electricity to tissue (optionally through the grip plates 42, 48), a frame supporting the electrode, and a blade slot 100A, 100B (see FIGS. 4C and 6A) configured to receive the blade 32 between the jaws 12.

In an example, the jaws 12A and 12B can each include an electrode configured to deliver electricity to tissue. In one example, the grip plates 42 and 44 can be the electrodes that are wired to a generator to apply the electricity to the tissue grasped between the two grip plates 42 and 44. The insulating portions 40 and 46 can connect the grip plates 42 and 44 to the jaw bodies 38 and 44 but keeps them electrically isolated. In one example, the insulating portions 40 and 46 can be coupled to the jaw bodies 38 and 44 and the grip plates 42 and 44 via, e.g., overmolding.

The top jaw 12A can include flanges 54A and 54B (collectively referred to as the flanges 54). An elongated body 58 can extend distally from the flanges 54. The flanges 54 can each include an opening 56A and 56B (collectively openings 56) that are configured to receive the pivot pin 52 such that the top jaw 12A can pivot relative the bottom jaw 12B and the outer shaft 28. The flanges 54 (which can be a set of flanges, that is, two flanges) can be rigid or semi-rigid members located at a proximal portion of the top jaw 12A. The flanges 54 of the top jaw 12A can each include projections 60A-1, 60A-2, 60B-1, and 6B-2 (collectively referred to as projections 60) that extend from the flanges 54. In an example, the projections 60 can extend from a bottom surface of the flanges 54. For example, flange 54A can include projections 60A-1 and 60A-2 and flange 54B can include projections 60B-1 and 60B-2. As discussed herein, these projections 60 are configured to engage the inner shaft 26 via the openings 80 along the projection 78 of the inner shaft 26. For example, the projections 60 can engage the inner shaft 26 such that as the inner shaft 26 is moved linearly, the linear motion is translated into a rotational motion to rotate the top jaw 12A relative the bottom jaw 12B and the outer shaft 28 between an open position and a closed position.

In an example, the flanges 54A and 54B can each include a shoulder 62A, 62B (collectively referred to as shoulders 62). In an example, the shoulders 62 can assist in limiting the rotation of the top jaw 12A. As discussed herein, as the top jaw 12A rotates about the bottom law 12B as the projections 60 engage with the openings 80 along the inner shaft 26, as rotation continues, the shoulders 62 will abut the openings 80 but will not extend through the openings 80.

The bottom jaw 12B can include the bottom machined bottom jaw 44, the bottom insulating portion 46, and the bottom grip plate 48. The bottom jaw 12B can include body portion 90 having a first wall portion 86 and a second wall portion 92. An elongated body 96 can extend distally from the body portion 90. Each of the first and second wall portions 86, 92 can include a pivot pin opening 98A, 98B that is configured to receive the pivot pin 52. As discussed herein, the bottom jaw 12B is rigidly coupled to the outer shaft 28 and coupled to the top jaw 12A via the pivot pin 52 such that the top jaw 12A can rotate from a closed position to an open position.

The bottom jaw 12B can include a body portion 90 and an elongated portion 96 extending distally from the body portion 90. The body portion 90 can have an opening 97 along the top surface 91 that is partially defined by a first wall 86 and a second wall 92. As seen in FIG. 5, the opening 97 is closed along a proximal end by a portion of the top surface 91 and is open along a distal end. The proximal end of the opening 97 is closed such that the bottom jaw 12B can contact and couple to the outer shaft 28 along 360 degrees of the circumference (or the entire perimeter). However, other configurations are possible and the contact between the bottom jaw 12B and the outer shaft 28 can be less than 360 degrees (less then the entire perimeter). As discussed herein, the opening 97 enables the flanges 54 of the top jaw 12A to be positioned laterally inward from the first and second walls 86, 96 of the bottom jaw 12B.

In an example, the bottom jaw 12B can include projections 93A and 93B (collectively projections 93) extending proximally into the opening 97, as seen in FIG. 6A. The projections 93 in combination with the first and second walls 86 and 92 form slots 95A and 95B (collectively slots 95) that receive the flanges 54 of the top jaw 12A. The gap 99 between the slots 95 form a portion of the blade channel 100B that can guide the blade 32 into the top and bottom jaws 12A and 12B.

As seen in FIGS. 6B and 6C, the bottom surface 106 and the side surface 107 can define openings 105A and 105B (collectively openings 105). A strut 104 can be positioned between the two openings 105. As discussed more herein, the openings 105 are configured to allow engagement and movement between the top jaw 12A and the inner shaft 26. In an example, a proximal portion of the elongate body 96 can define an inner shoulder 102 that can assist in limiting the distal translation of the inner shaft 26. For example, as the inner shaft 26 is translated distally along the longitudinal axis A1, a distal end 79 (see FIGS. 7A & 7B) of the inner shaft 26 can contact the inner shoulder 102 to limit the distal translation. However, other configurations, alone or in combination with the inner shoulder 102, can be used for limiting the distal translation of the inner shaft 26.

Figure 7A:
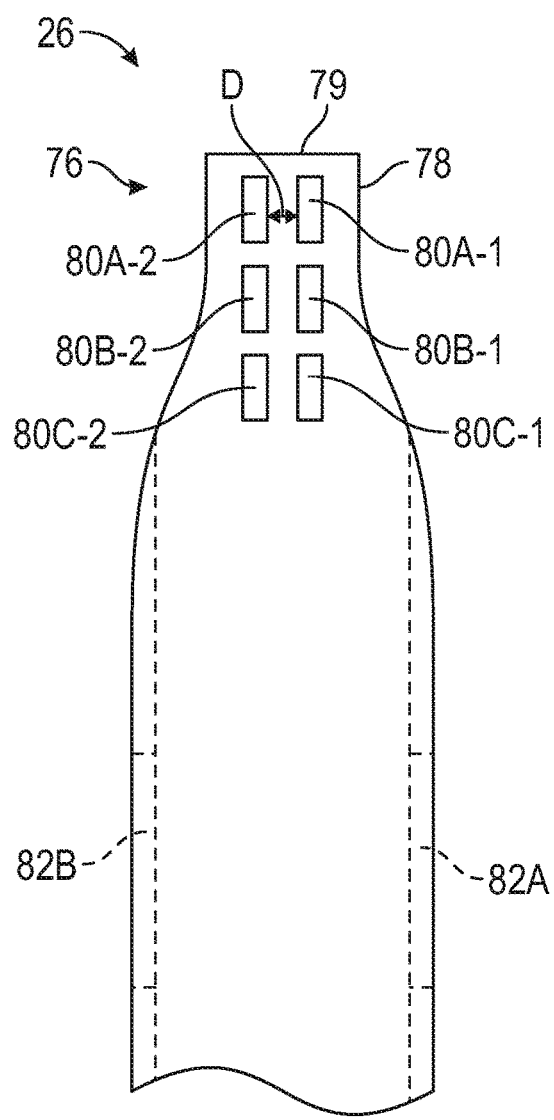
FIG. 7A illustrates bottom-up view of the inner shaft, in accordance with at least one example of this disclosure.
Figure 7B:
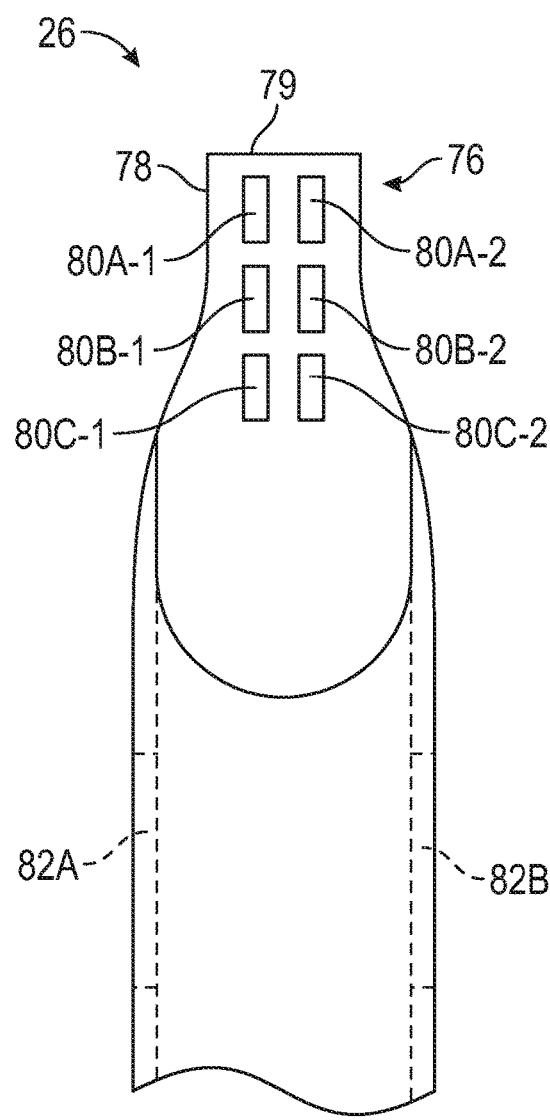
FIG. 7B illustrates a top-down view of the inner shaft shown in FIG. 7A.

Referring to FIGS. 7A and 7B, the inner shaft 26 is shown according to one example embodiment. FIG. 7A illustrates a bottom-up view of the inner shaft 26 and FIG. 7B illustrates a top-down view of the inner shaft 26. As discussed herein, the inner shaft 26 can include the axial tracks 82A and 82B that can receive the guide 50 such that the inner shaft 26 can move relative to the guide 50. The distal portion 76 can include the projection 78 that includes at least one set of openings 80A-1 and 80A-2 (collectively openings 80A). As discussed herein, the openings 80A are configured to receive the projections 60 located on the top jaw 12A. As shown in FIGS. 7A and 7B, the inner shaft 26 includes three sets of openings 80A-1 and 80A-2 (collectively openings 80A), 82B-1 and 82B-2 (collectively openings 80B), and 83C-1 and 83C-2 (collectively openings 80C), where all three sets of openings (80A, 80B, and 80C) are collectively referred to as openings 80. Generally, projections 60A-1 and 60B-1 of the top jaw 129 can be positioned within the openings 80A-1 and 80A-2. As linear motions is applied to the inner shaft 26, the upper jaw 12A rotates and projections 60A-2 and 60B-2 become engaged with openings 80B-1 and 80B-2 as the upper jaw 12A transitions from the closed position to the open position. Once the distal translation of the inner shaft 26 is stopped, e.g., once a distal end 79 of the projection 78 contacts the inner shoulder 102 of the bottom jaw 12B (see FIG. 6B), the shoulders 62A and 62-B can abut the third set of openings 80C-1 and 80C-2.

As shown in FIGS. 7A and 7B, the openings of each set of openings 80A, 80B, and 80C are spaced apart by a distance D. In an example, the distance D between the openings 80A-1 and 80A2, openings 80B-1 and 80B-2, and openings 80C-1 and 80C-2, can be sufficient such that an appropriate amount of the opening 80 can be exposed beyond the strut 104 (see FIG. of the bottom jaw 12B so that the openings 80A can receive the projections 60 of the top jaw 12A.

While shown with the top jaw 12A including two sets of projections 60 and the inner shaft 26 including three set of openings 80, other configurations are contemplated. In one example, the top jaw 12A could include one projection that could engage with one opening on the inner shaft 26. For example, projection 60A-1 could engage with one opening 80A-1. In other examples, instead of three sets of openings 80A, 80B, and 80C, the inner shaft 26 can include one or more separate single openings. For example, openings 80A-1 and 80A-2 could be a single opening, openings 80B-1 and 80B-3 could be a single opening, and/or openings 80C-1 and 80C-2 could be a single opening. Thus, there would be one to three separate openings extending along the longitudinal axis A1.

Figure 8B:
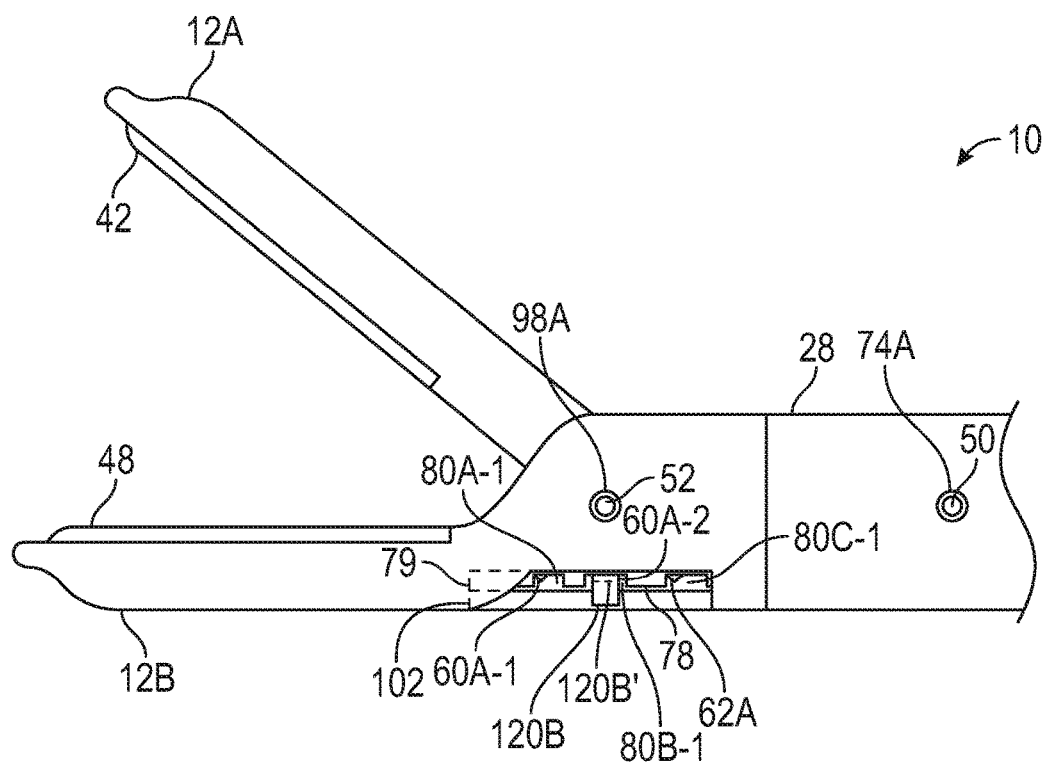
FIG. 8B illustrates a side-view of the end effector of the forceps in FIG. 8A showing the jaws in an open position.
Figure 8C:
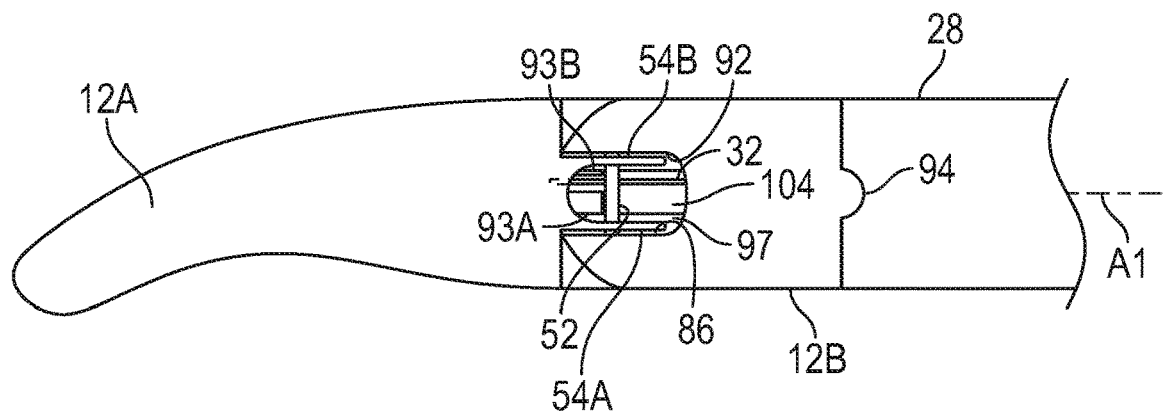
FIG. 8C illustrates a top-down view of the end effector of the forceps in FIG. 8A.
Figure 8D:
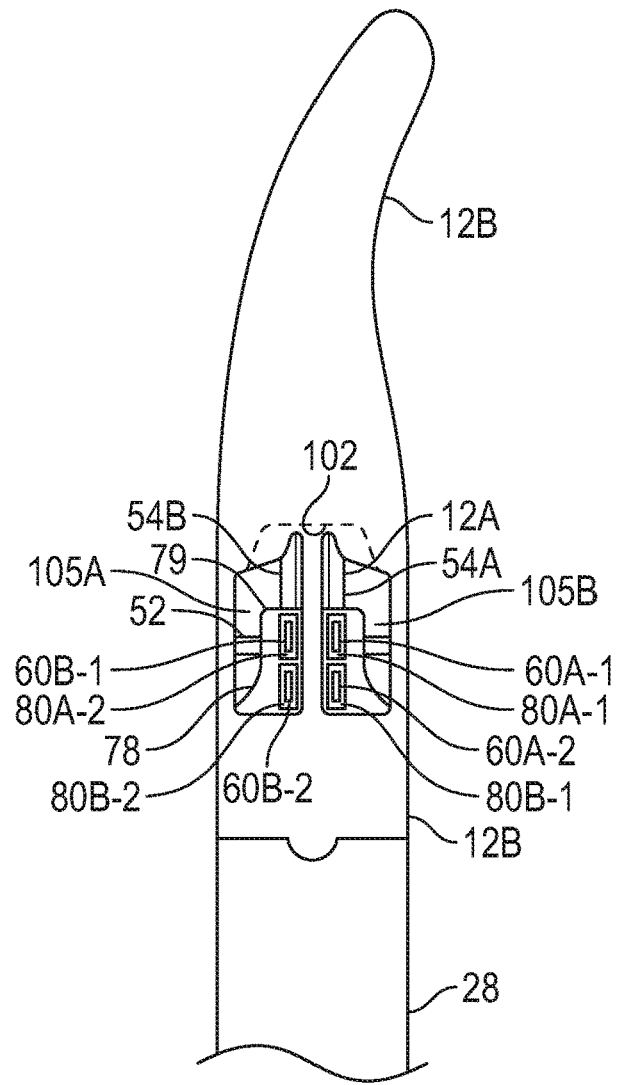
FIG. 8D illustrates a bottom-up view of the end effector of the forceps in FIG. 8A.
Figure 9:
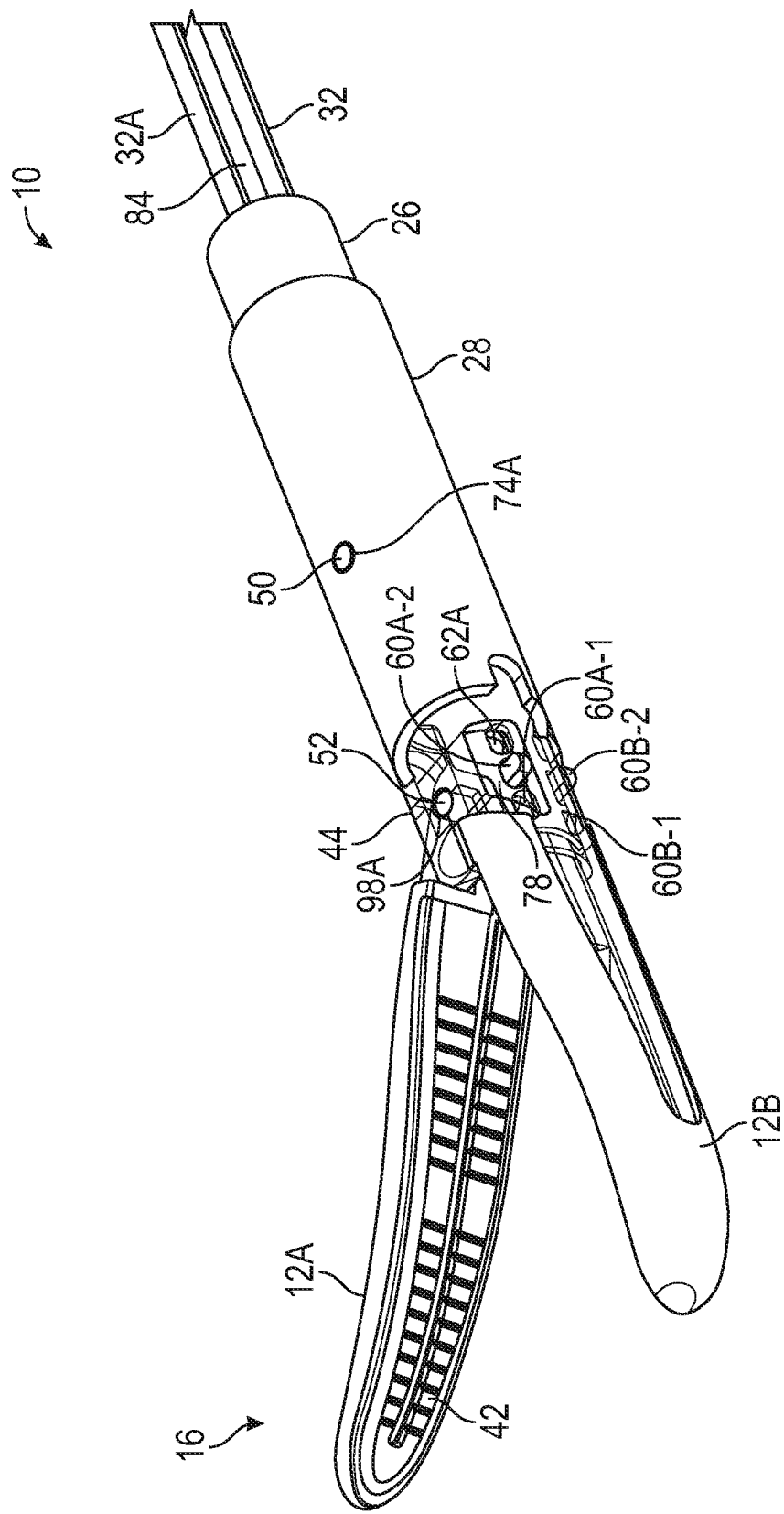
FIG. 9 illustrates a perspective view of the end effector of the forceps showing the jaws in an open position, in accordance with at least one example of this disclosure.

FIGS. 8-9 illustrate an assembled view of a portion of the forceps 10 including the end effector 16. FIG. 8A illustrates a side-view of the end effector 16 where the jaws 12 are in a closed position. FIG. 8B illustrates the side-view of the end effector 16 in FIG. 8A but the jaws 12 are in an open position. FIG. 8C illustrates a top-down view of the portion of the forceps 10 where the jaws 12 are in a closed position. FIG. 8D illustrates a bottom-up view of the portion of the forceps 10 in FIG. 8B. FIG. 9 illustrates a perspective view of a portion of the forceps 10 with a portion of the jaw body 44 of the bottom jaw 12B being translucent.

As seen in FIG. 8A, the jaws 12 are in a closed position. The bottom jaw 12B is coupled to the outer shaft 28 and the top jaw 12B is rotationally coupled to the bottom jaw 12B via the pivot pin 52. In the closed position, the projection 60A-1 extends through a respective opening 80A-1 of the inner shaft 26. While not shown in FIG. 8A, projection 60B-1 can also extend through a respective opening 80A-2. A bottom surface 120A of the projection 60A-1 does not extend past the outer diameter of the jaws 12 or the outer shaft 28. Further, a portion of projection 60A-2 is partially inserted into opening 80B-1. Similarly, while not shown in FIG. 8A, a portion of projection 60B-2 is partially inserted into opening 80B-2. As discussed herein, to open the jaws 12 distally translating the inner shaft 26 can cause the top jaw 12A to rotate about the pivot pin 52 and relative to the bottom jaw 12B. As the inner shaft 26 is moved distally, a distal surface of projection 60A-1 contacts a proximal surface of opening 80A-1 as rotation of the top jaw 12A begins. As seen in FIG. 8A, the pivot pin 52 and the guide 50 can be positioned along the longitudinal axis A1.

As seen in FIG. 8A, there is a vertical offset V1 between the pivot axis (pivot pin 52) and the line of action of the projection 78 of the inner shaft 26. The vertical offset V1 between the pivot axis of the pivot pin 52 and the line of action of the projection 78 can be such that both are below or above the longitudinal axis or where one is above the longitudinal axis A1 and the other is below the longitudinal axis A1. As seen in FIG. 8A, the pivot pin 52 is located along the longitudinal axis A1 and the line of action of the projection 78 is below the longitudinal axis A1.

As seen in FIG. 8A, the bottom surface 120A of the projection 60A-1 extends through the thickness of the inner shaft 26 and into the thickness of the outer shaft 28. That is, the bottom surface 120A does not extend beyond an outer surface (the periphery) of the outer shaft 28. In another example, a modified bottom surface 120A' of the projection 60A-1 can extend into the thickness of the inner shaft 26. That is, the bottom surface 120A' would not extend past an outer surface (the periphery) of the inner shaft 26. Thus, in that instance, the bottom surface 120A' would not extend beyond the inner surface or the outer surface (outer periphery) of the outer shaft 28.

FIGS. 8B and 9 illustrates the jaws 12 in an open configuration. The distal end 79 of the projection 78 can contact inner shoulder 102 of the bottom jaw 12B to limit distal translation of the inner shaft 26. In this position, the projection 60A-2 can extend through opening 80B-1. While not shown in FIG. 8B, projection 60B-2 can extend through opening 80B-2 and the shoulder 62A can abut a distal surface defining opening 80C-1. A bottom surface 120B of projection 60A-2 does not extend past the outer diameter of the jaw 12 or the outer diameter (outer surface or periphery) of the outer shaft 26. Thus, even in the open position, the bottom surface 120A does not extend past the outer diameter (outer surface or periphery) of the outer shaft 26. In another example, a modified bottom surface 120B' of the projection 60B-1 can extend into the thickness of the inner shaft 26. That is, the bottom surface 120B' would not extend past the outer surface (the periphery) of the inner shaft 26. Thus, in that instance, the bottom surface 120B' would not extend beyond the inner surface or the outer surface (outer periphery) of the outer shaft 28.

As discussed herein, minimizing or preventing components of the forceps 10 extending beyond the diameter of the outer shaft 28 can prevent damage to surrounding tissue.

To close the jaws 12, proximal linear motion can be applied to the inner shaft 26. In doing so, a proximal side of the projection 60A-2 engages a distal side of a portion of the inner shaft 26 that defines opening 80B-1 and the top jaw 12A begins to close until the top jaw 12A is at the closed position, as shown in FIG. 8A.

FIG. 8C illustrates a top-down view of the portion of the forceps 10 where the jaws 12 are in a closed position. For simplicity, the inner shaft 26 is not shown. As seen in FIG. 8C, the flanges 54A and 54B of the top jaw 12A are positioned laterally inward of the first wall 86 and the second wall 92 of the bottom jaw 129. The blade 32 is position laterally inward of the flanges 54A and 54B. The blade 32 can reciprocate between the two flanges 54A and 54B of the top jaw 12A. Thus, the two flanges 54A and 549 can provide a channel for the centrally located blade 32 to reciprocate.

FIG. 8D illustrates a bottom-up view of the portion of the forceps 10 where the jaws 12 are in a closed position. As seen in FIG. 8D, the distal end 79 of the projection 78 is spaced apart from the inner shoulder 120 of the bottom jaw 12B when the jaws 12 are in a closed position. The projections 60 are positioned adjacent and within respective openings 80.

In operation of some examples, a handle (such as those discussed above) can be operated to translate the inner shaft 26 within (and with respect to) the outer shaft 28. For example, distal translation of the inner shaft 26 with respect to the outer shaft 28 can cause the jaws 12 to move from a closed position (as shown in FIG. 8A) to an open position (as shown in FIGS. 1, 8B, and 9). Conversely, proximal translation of the inner shaft 26 can cause the jaws 12 to move from an open position to the closed position, such that the translation of the inner shaft 26 can translate the top jaw 12A to rotate relative to the bottom jaw 129.

More specifically, in one example, distal translation of the inner shaft 26 can cause the projections 60 on the flanges 54 of the top jaw 12A to engage with the openings 80 positioned along the inner shaft 26. Because the projections 60 are engaged with the openings 80 and that the top jaw 12A is coupled to the bottom jaw 12B via the pivot pin 52, distal translation of the inner shaft 26 causes the top jaw 12A to open and rotate about the pivot pin 52. That is, as the projections 60 move distally with the distal movement of the inner shaft 26 and because the top jaw 12A is fixed/coupled to the pivot pin 52, the top jaw 22 opens or rotates relative to the bottom jaw 12B toward (an ultimately into) an open position.

Distal translation of the inner shaft 26 can be limited by contact between the guide 50 and a proximal end of each of the axial tracks 82 (as shown in FIG. 2). In some examples, distal translation of the inner shaft 26 can be limited by contact between a distal end 79 of the inner shaft 26 and a portion of the bottom jaw 12B such as the inner shoulder 102 (see FIG. 89). In some example, the distal translation of the inner shaft 26 can be limited by contact between the shoulders 62 of the flanges 54 and openings (e.g., openings 80C) along the projection 78 of the inner tube 26.

To close the jaws, the inner shaft 26 can be translated proximally, which causes the projections 60 to translate proximally. As the projections 60 translate proximally, the top jaw 12A rotates about the pivot pin 52 from the open position toward (an ultimately into) a closed position). Proximal translation of the inner shaft 26 can be limited by contact between the guide 50 and a distal end of each of the axial tracks 82. In other examples, proximal translation of the inner shaft 26 can be limited by contact between the top jaw 12A and the bottom jaw 12B.

FIGS. 10-18 illustrate another example forceps 210 of the present disclosure. The forceps 210 are similar to forceps 10 (shown in FIGS. 1-9) but forceps 210 include a different an end effector 220 and a different reciprocating inner shaft. For example, forceps 210 includes a drive bar 214 that includes a drive bar shaft 240 and a drive bar strut 242. The forceps 210 can include a handpiece 14, one or more actuators 20, an outer shaft 212 (or outer tube), the drive bar 214, and an end effector 220. The drive bar 214 can be referred to as an inner shaft; however, the drive bar 214 is formed from two pieces whereas the inner shaft 26 of FIG. 1 is a single piece. However, both inner shaft 26 of forceps 10 (shown in FIG. 1) and drive bar 214 of forceps 210, translate linear motion into rotational motion to rotate the top jaw member of the end effector from a closed position to an open position.

The forceps 210 can include the handpiece 14 at a proximal end and the end effector 220 at a distal end. An intermediate portion 218 can extend between the handpiece 14 and the end effector 220 to operably couple the handpiece 14 to the end effector 16. Various movements of the end effector 220 can be controlled by one or more actuation systems 20 of the handpiece 14. In the illustrative example, the end effector 220 can include a top jaw 222A and a bottom jaw 222B (collectively referred to as jaws 222) that are capable of moving between an open position and a closed position. The end effector 220 can be rotated along a longitudinal axis A2 of the forceps 210. The end effector 220 can include a cutting blade and an electrode for applying electrosurgical energy.

Figure 10:
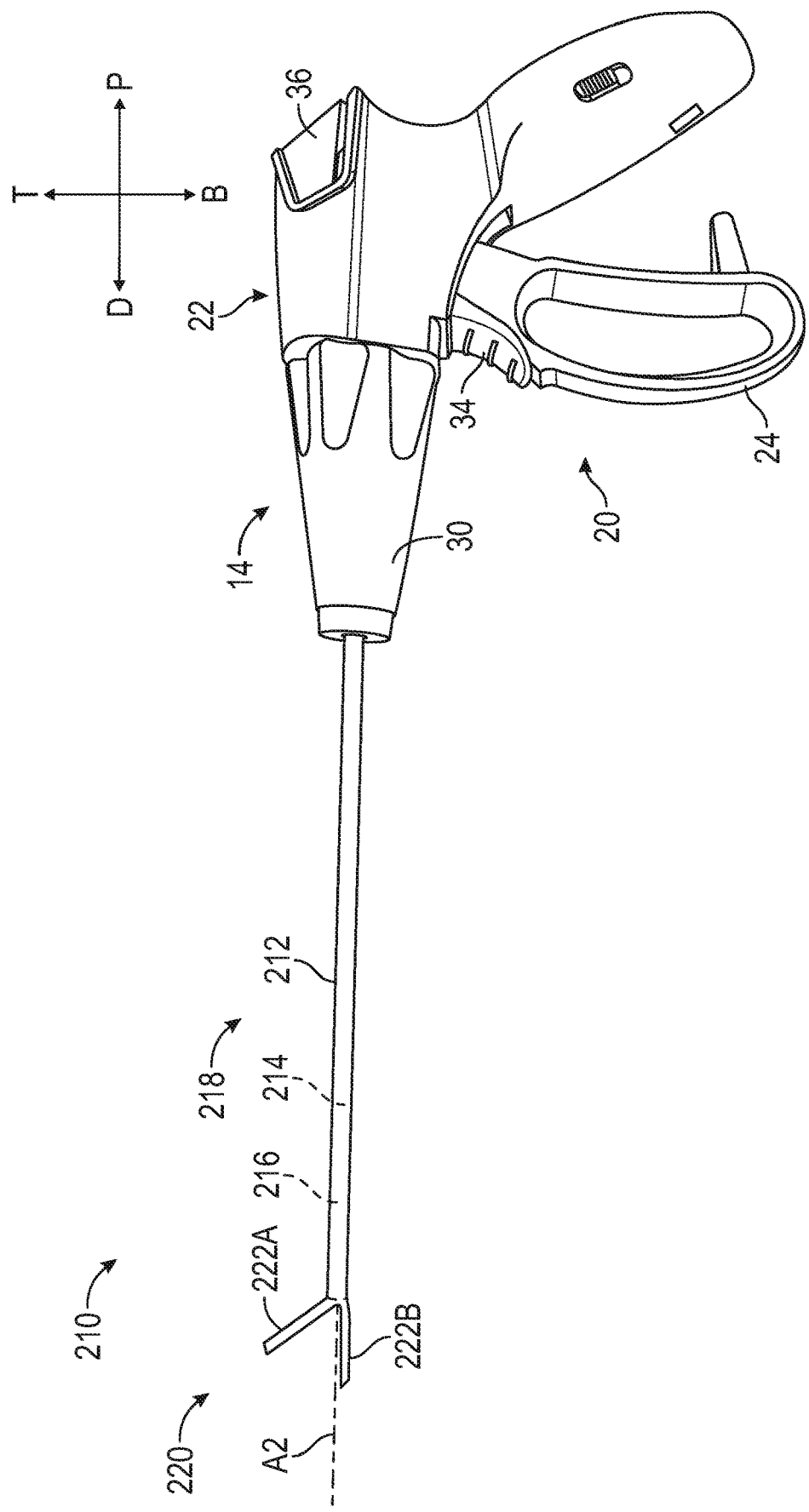
FIG. 10 illustrates a side view of a forceps showing jaws in an open position, in accordance with at least one example of this disclosure.

As broadly shown in FIG. 10, the forceps 210 can include the jaws 222, the housing 22, the lever 24, the drive bar 214, the outer shaft 212, a rotational actuator 30, a blade assembly 216 (including a blade shaft 254A and a cutting blade 254B of FIG. 2), the trigger 34, and an activation button 36. In this example, the end effector 220, or a portion of the end effector 220 can be one or more of: opened, closed, rotated, extended, retracted, and electrosurgically energized.

Figure 17A:
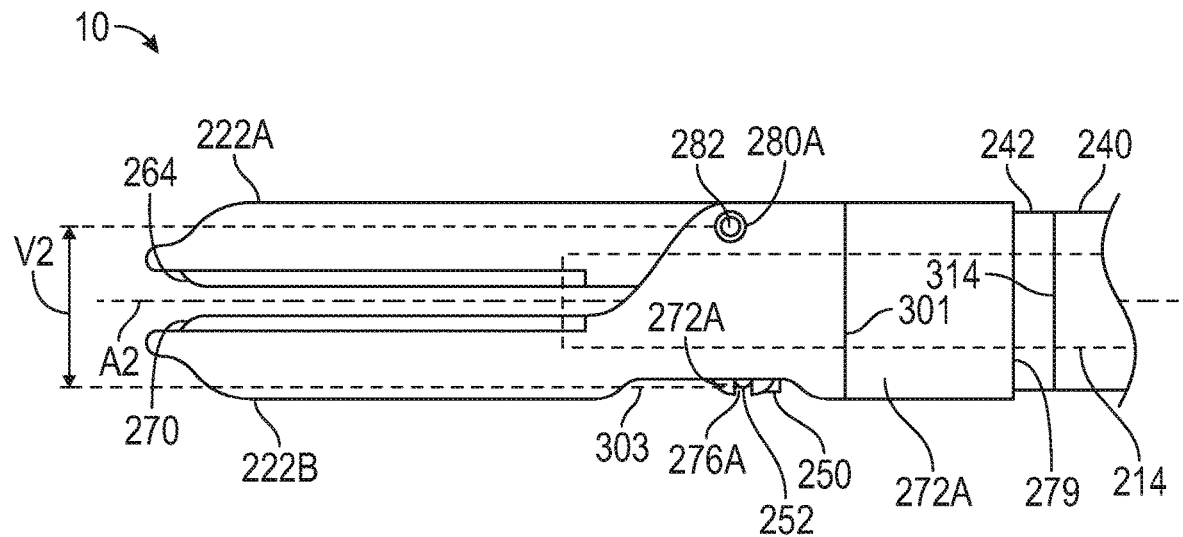
FIG. 17A illustrates a side-view of the end effector of the forceps showing the jaws in a closed position, in accordance with at least one example of this disclosure.

To operate the end effector 220, the user can displace the lever 24 proximally to drive the jaws 222 from the open position (FIG. 10) to the closed position (FIG. 17A). In the example of forceps 210, moving the jaws 222 from the open position to the closed position allows a user to clamp down on and compress a tissue. The handpiece 14 can also allow a user to rotate the end effector 220. For example, rotating rotational actuator 30 causes the end effector 220 to rotate by rotating both the drive bar 214 and the outer shaft 212 together.

In some examples, with the tissue compressed, a user can depress the activation button 36 to cause an electrosurgical energy to be delivered to the end effector 220, such as to an electrode. Application of electrosurgical energy can be used to treat the tissue such as seal or otherwise affect the tissue being clamped. In some examples, the electrosurgical energy can cause tissue to be sealed, ablated, and/or coagulated. Example electrodes such as the grip plates are described herein, but electrosurgical energy can be applied to any suitable electrode.

In some examples, the forceps 210 can be used to cut the treated tissue via the blade assembly 216 (or blade 216). For example, the handpiece 14 can enable a user to extend and retract the cutting blade 254A attached to a distal end of the blade shaft 254A (FIG. 2). The cutting blade 254A can be extended by displacing the trigger 34 proximally. The cutting blade 254A can be retracted by allowing the trigger 34 to return distally to a default position. The default position of the trigger 34 is shown in FIG. 10. In some examples, the handpiece 14 can include features that inhibit the blade 254A from being extended until the jaws 222 are at least partially closed, or fully closed.

The forceps 210 can be used to perform a treatment on a patient, such as a surgical procedure. In an example, a distal portion of the forceps 10, including the jaws 222, can be inserted into a body of a patient, such as through an incision or another anatomical feature of the patient's body. While a proximal portion of the forceps 210, including the housing 22 remains outside the incision or another anatomical feature of the body. Actuation of the lever 24 causes the jaws 222 to clamp onto a tissue. The rotational actuator 30 can be rotated via a user input to rotate the jaws 222 for maneuvering the jaws 222 at any time during the procedure. Activation button 36 can be actuated to provide electrical energy to jaws 222 to cauterize or seal the tissue within the closed jaws 12. Trigger 34 can be moved to translate the blade 32 distally in order to cut the tissue within the jaws 22.

The components of the forceps 210 can each be comprised of materials such as one or more of metals, plastics, foams, elastomers, ceramics, composites, combinations thereof, or the like. Materials of some components of the forceps are discussed below in further detail.

Figure 11:
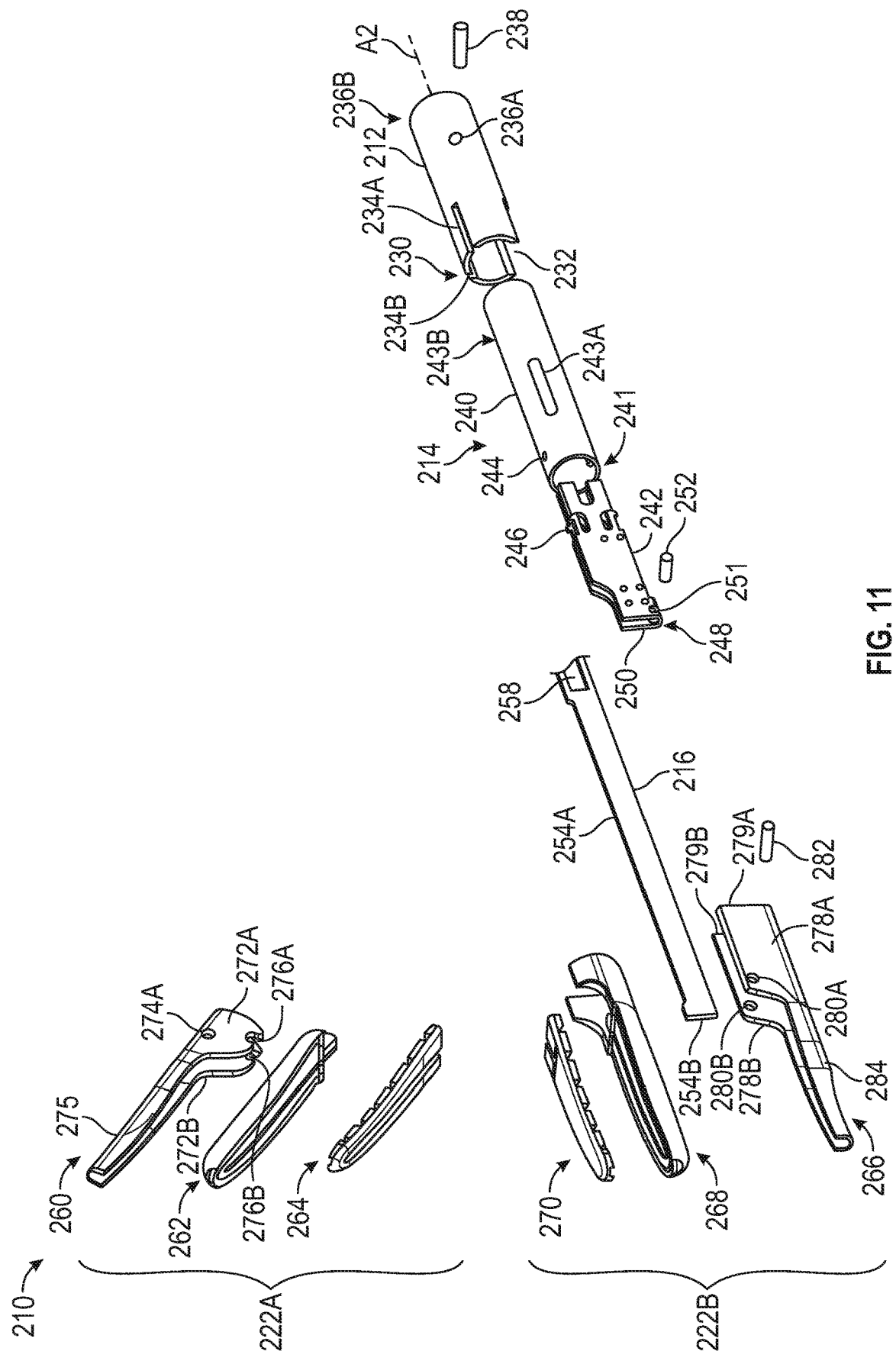
FIG. 11 illustrates an expanded view of a portion of the forceps, in accordance with at least one example of this disclosure.

FIG. 11 illustrates an expanded view of a portion of the forceps 210. The forceps 210 can include the top jaw 222A, the bottom jaw 222B, the drive bar 214, the outer shaft 212, the blade 216, a guide (or proximal pin) 238, a drive pin 252, and a pivot pin 282. As discussed herein, the bottom jaw 222B can be stationary and is rigidly coupled to a distal portion 230 of the outer shaft 212. The top jaw 222A can be moveable and is pivotably coupled to the bottom jaw 222B and the outer shaft 212. The top jaw 222A can be engaged with a portion of the drive shaft 214 such that translation of the drive shaft 214 along the longitudinal axis A2 can pivot the top jaw 222A relative to the bottom jaw 222B. That is, the linear movement of the drive shaft 214 can be translated into rotational motion to rotate the top jaw 222A about pivot pin 282 from a closed position to an open position.

The outer shaft 212 can be a rigid or semi-rigid and include an elongate body having a geometric shape of a cylinder. The drive bar 214 can be a rigid or semi-rigid and includes the drive bar shaft 240 (or drive bar tube) and a drive bar strut 242 coupled to a distal portion 241 of the drive bar shaft 240.

In some examples, the drive bar shaft 240 can have a shape matching the shape of the outer shaft 212, such as the geometric shape of a cylinder. In some examples, the drive bar shaft 240 and the outer shaft 212 can have other shapes such as an oval prism, a rectangular prism, a hexagonal prism, an octagonal prism, or the like. In some examples, a portion of the drive bar shaft 240 and a corresponding portion of the outer shaft 212 can have a non-rotational shape. That is, while the drive bar shaft 240 can be moved relative to the outer shaft 212 along the longitudinal axis A2, the drive bar shaft 240 and the outer shaft 212 are rotationally coupled or rotationally locked. Therefore, rotational motion applied to one of the drive bar shaft 240 will rotate the outer shaft 212 and rotational motion applied to the outer shaft 212 will rotate the drive bar shaft 240. In some examples, the shape of the drive bar shaft 240 can be different from the shape of the outer shaft 212

The outer shaft 212 can extend from a proximal portion to a distal portion 230 along the longitudinal axis A2. Similarly, the drive bar shaft 240 can extend from a proximal portion to a distal portion 241 along the longitudinal axis A1 In an example, the longitudinal axis A2 can be a central axis of one or more of the drive bar shaft 240 and the outer shaft 212. The drive bar shaft 240 can include an axial bore extending along the longitudinal axis A2. The outer shaft 212 can also include an axial bore extending along the longitudinal axis A2. The drive bar shaft 240 and the drive bar strut 242 can have an outer dimension (such as an outer diameter) smaller than an inner diameter of the outer shaft 212 such that the drive bar shaft 240 and the drive bar strut 242 can be positioned within the outer shaft 212 and can be translatable therein along the longitudinal axis A2.

As discussed herein, the outer shaft 212 can be coupled to the bottom jaw 222B. In an example, the distal portion 230 of the outer shaft 212 can include one or more recesses 232 and/or one or more slots 234A and 234B (collectively slots 234) that can receive a corresponding portion of the bottom jaw 2229. While a recesses/slots are shown, any mechanism to rotationally lock and linearly lock the outer shaft 212 to the bottom jaw 222B is contemplated.

The drive bar shaft 240 can extend from a proximal portion to a distal portion 241. The drive bar strut 242 is coupled to the distal portion 241 of the drive bar shaft 240. For example, the drive bar shaft 240 can include one or more openings 244 located along the top and bottom of the drive bar shaft 240. Projections 246 located along the drive bar strut can be coupled with the openings 244. For example, as the drive bar strut 242 is inserted into the distal end 241 of the drive bar shaft 240, the projections 246 can flex inward toward the longitudinal axis A2 and expand out and into a respective opening 244. The drive bar strut 242 extends from a proximal portion to a distal portion 248. A drive pin portion 250 can be positioned at the distal portion 24 of the drive bar strut 242. The drive bar portion 250 defines an opening 251 that can receive the drive pin 252

The blade 216 can be an elongate cutting member including the blade shaft 254A and have one or more sharpened edges (cutting blade 254B) configured to cut or resect tissue or other items. The blade 216 can be located within the outer shaft 212 (and within the drive bar 240) and can extend along (and optionally parallel with) the longitudinal axis A2. The blade 216 can be translatable with respect to the drive bar 214 and the outer shaft 212 to extend between (or into) the top jaw 222A and the bottom jaw 222B. In some examples, the blade 216 can extend axially through the drive bar 214 offset from the longitudinally axis A1.

The guide 238, the pivot pin 282, and the drive pin 252 can each be a rigid or semi-rigid pin, such as a cylindrical pin. The guide 238, the pivot pin 282, and the drive pin 252 can have other shapes in other examples, such as rectangular, square, oval, or the like. In some examples, each pin can be the same size (e.g. diameter and length) to simplify manufacturing and reduce cost. Each pin can have a smooth surface to help reduce surface friction between the pins and components of the forceps 210, such as between the pivot pin 282 and the jaws 222, between the guide 238 and the drive bar 240 and the blade 216, and between the drive pin 252 and the drive bar strut 246 and the first jaw 222A. In some examples, each of the guide 238, the pivot pin 282, and the drive pin 252 can be other components such as one or more projections, bosses, arms, or the like.

The outer shaft 212 can include includes openings 236A and 236B (only one opening 236B is visible in FIG. 11; collectively referred to as openings 236) on opposite sides of the outer shaft 212 to receive the guide 238. The guide 238 can be secured to the outer shaft 212 such as by insertion into openings 236.

The drive bar shaft 240 can include a pair of axial tracks 243A and 243B (only one axial track 243A is visible in FIG. 11; collectively referred to as axial tracks 243) located on opposite sides of the drive bar shaft 240. The pair of axial tracks 243 arranged to receive the guide 238 therein. As discussed herein, the drive bar shaft 240 is moveable relative to the guide 50 as the drive bar 214 translates relative to the outer shaft 212. The axial tracks 243 can each be axial slots extending laterally through walls of the drive bar shaft 240. In other example, the axial tracks 243 can be channels, grooves, recesses, or other guides configured to receive a guiding member. In some examples, the axial tracks 243 do not extend entirely through the inner shaft 2026.

The axial tracks 243 can be sized and shaped to receive the guide 50 therein and can be sized and shaped for the guide 50 to translate within the axial tracks 243 between a proximal edge and a distal edge of the axial tracks 243. Distal translation of the drive bar 214 relative to the outer shaft 212 can be limited, for example, by contact between the guide 238 and the proximal edges of the respective axial tracks 243. However, other configurations for limiting the distal translation of the drive bar 214 are contemplated.

The blade 216 can include an axial opening 258 extending along the blade shaft 254A. The axial opening 258 is sized and shaped to receive the guide 50. As the blade 216 translates relative to the outer shaft 212 and the drive bar 214, the axial opening 258 receives and moves relative to the guide 50. As discussed herein, the pivot pin 282 and the drive pin 252 are spaced from the longitudinal axis A2 such that the blade shaft 254A can translate between them as the blade 216 is moved distally and extends into the jaws 222. That is, the blade 216 is positioned between the pivot pin 282 and the drive pin 252.

The axial opening 258 of the blade 216 extends from a distal edge to a proximal edge. Distal translation of the blade 216 can be limited, for example, by contact between the guide 50 and the proximal edge of the axial opening 258. However, other configurations for limiting the distal translation of the blade 216 are contemplated.

Figure 12:
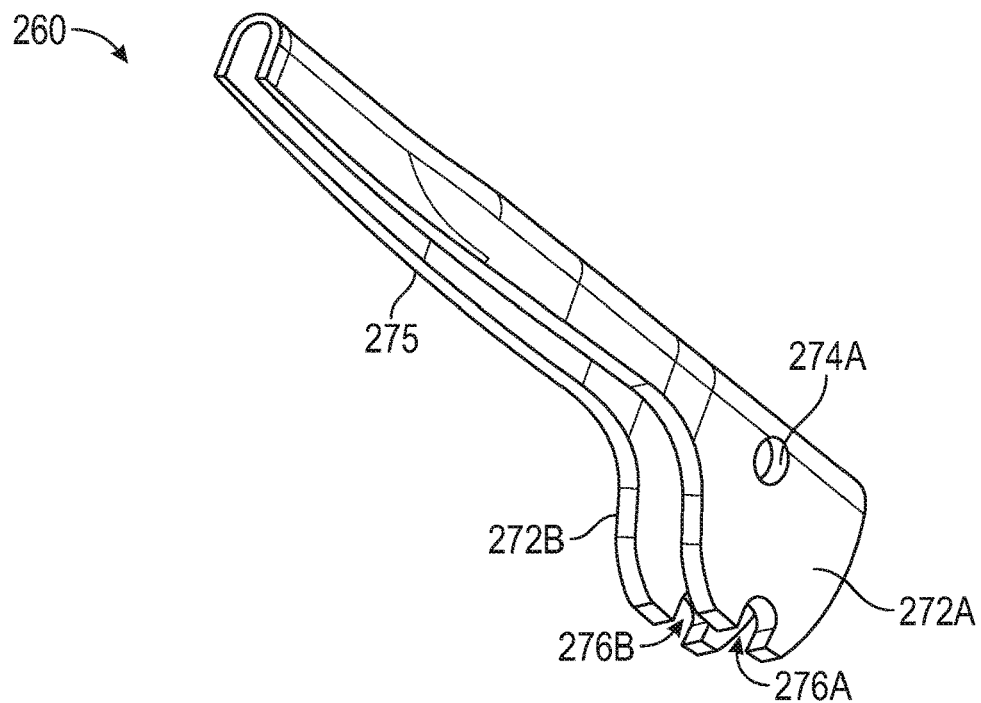
FIG. 12 illustrates a perspective view of a jaw body of the top jaw, in accordance with least one example of this disclosure.
Figure 13A:
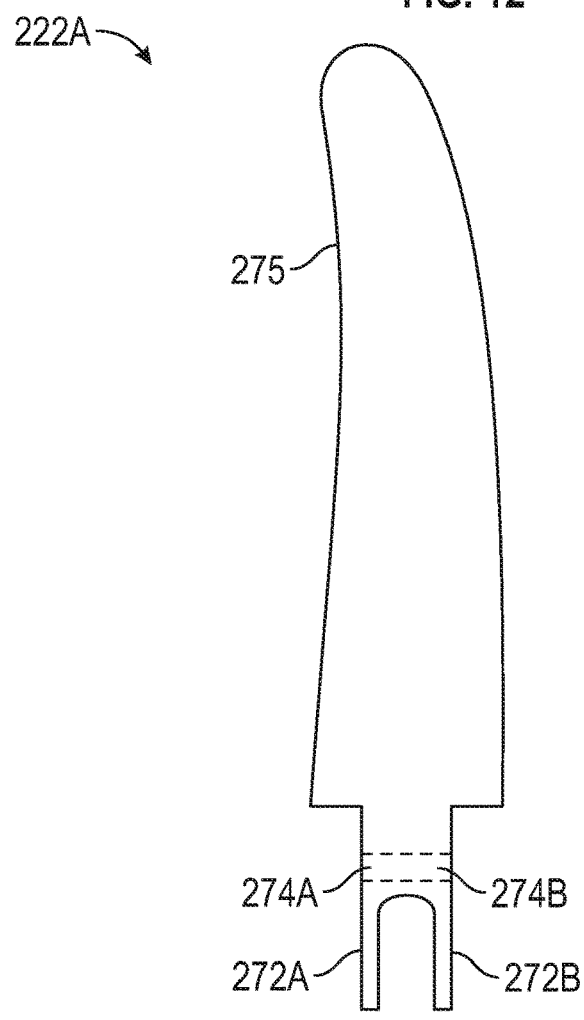
FIG. 13A illustrates a top-down view of the top jaw, in accordance with at least one example of this disclosure.
Figure 14:
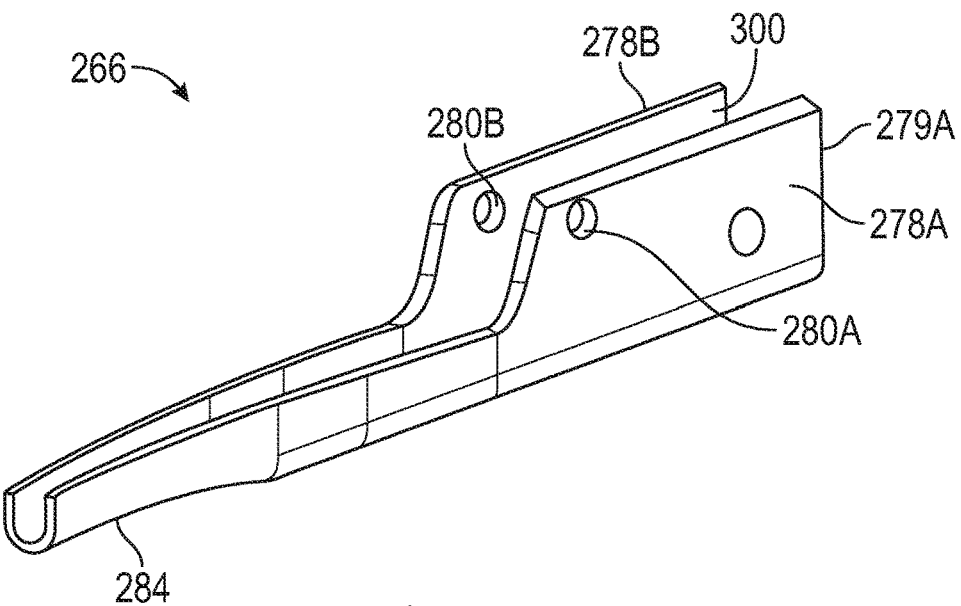
FIG. 14 illustrates a perspective view of a jaw body of the bottom jaw, in accordance with least one example of this disclosure.
Figure 15A:
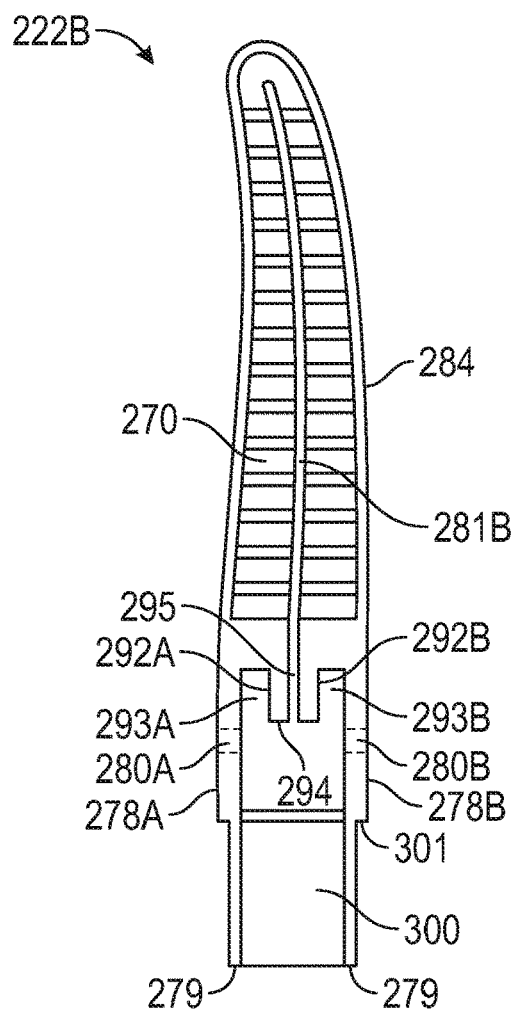
FIG. 15A illustrates a top-down view of the bottom jaw, in accordance with at east one example of this disclosure.
Figure 15B:
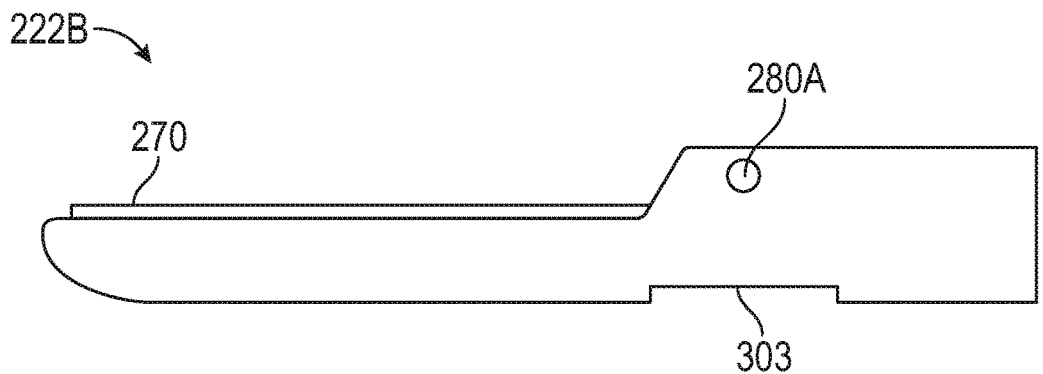
FIG. 15B illustrates a side-view of the bottom jaw shown in FIG. 15A.
Figure 15C:
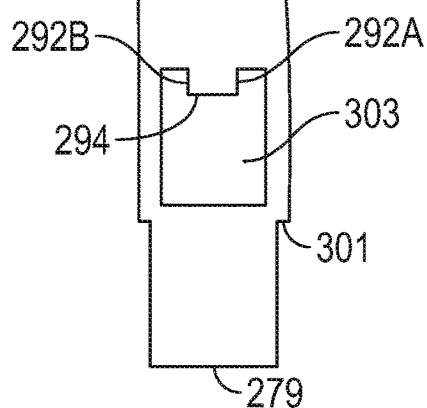
FIG. 15C illustrates a bottom-up view of the bottom jaw shown in FIGS. 15A-B.
Figure 15D:
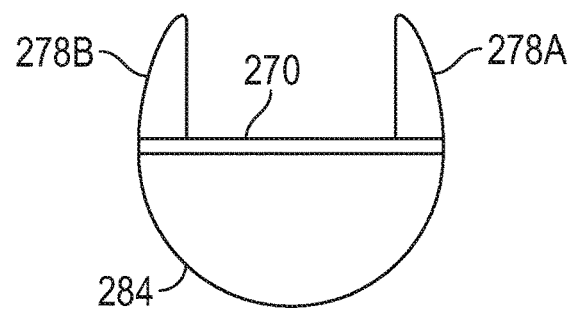
FIG. 15D illustrates a distal view of the bottom jaw shown in FIG. 15A-C.
Figure 15E:
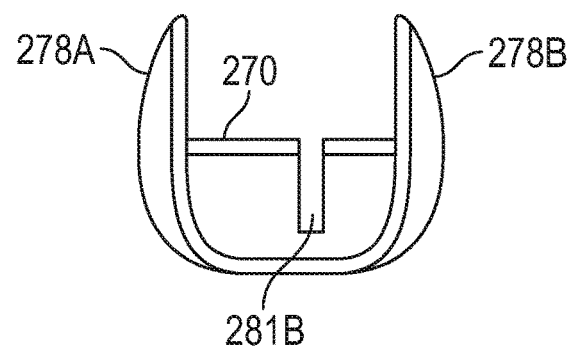
FIG. 15E illustrates a proximal view of the bottom jaw shown in FIGS. 15A-6D.

FIGS. 12-13E illustrate views of the top jaw 222A and FIGS. 14-15E illustrate views of the bottom jaw 222B. In particular, FIG. 12 illustrates a perspective view of a jaw body 260 of the forceps 10, FIG. 13A illustrates a top down view of top jaw 222A, FIG. 13B illustrates a side-view of the top jaw 222A, FIG. 13C illustrates a bottom-up view of the top jaw 222A, FIG. 13D illustrates a front view or distal view of the top jaw 222A, and FIG. 4E illustrates a back-end view or proximal view of the top jaw 222A. FIG. 14 illustrates a perspective view of a jaw body 266 of the forceps 10, FIG. 15A illustrates a top down view of the bottom jaw 222B, FIG. 15B illustrates a side-view of the bottom jaw 222B, FIG. 15C illustrates a bottom-up view of the bottom jaw 2229, FIG. 15D illustrates a front view or distal view of the bottom jaw 222B, and FIG. 15E illustrates a back-end view or proximal view of the bottom jaw 222B.

The forceps 210 will now be discussed referencing FIGS. 10-15E. The end effector 220 can include the top jaw 222A and the bottom jaw 222B (collectively referred to herein as jaws 12). The top jaw 222A can include a top jaw body 260 (or jaw body 260), a top insulating portion 262, and a top grip plate 264. The bottom jaw 222B can include a bottom jaw body 266 (or jaw body 266), a bottom insulating portion 268, and a bottom grip plate 270. The combination of the jaw body 260, the top insulating portion 262, and the top grip plate 264 form the top jaw 222A. Similarly, the combination of the jaw body 266, the bottom insulating portion 268, and the bottom grip plate 270 form the bottom jaw 12B. While illustrated as separate components, one or more of the jaw body, insulating portions, and grip plates of each respective jaw can be formed as one integral component.

In an example, the jaws 222A and 222B can each include an electrode configured to deliver electricity to tissue. In one example, the grip plates 264 and 266 can be the electrodes that are wired to a generator to apply the electricity to the tissue grasped between the two grip plates 264 and 266. The insulating portions 262 and 268 can connect the grip plates 264 and 266 to the jaw bodies 260 and 270 but keeps them electrically isolated. In one example, the insulating portions 262 and 268 can be coupled to the jaw bodies 260 and 270 and the grip plates 264 and 266 via, e.g., overmolding.

The grip plates 264 and 266 of the jaws 222 can each be a rigid or semi-rigid member configured to engage tissue and/or the opposing jaw to grasp tissue, such as during an electrosurgical procedure. One or more of the grip plates 264, 270 can include one or more of serrations, projections, ridges, or the like configured to increase engagement pressure and friction between the grip plates 264, 270 and tissue. The jaws 222 can each include an electrode configured to deliver electricity to tissue (optionally through the grip plates 264, 270), a frame supporting the electrode, and a blade slot 281A and 281B (see FIGS. 13C and 15A) configured to receive the blade 216 between the jaws 222.

The top jaw 222A can include flanges 272A and 272B (collectively referred to as the flanges 272). An elongated body 275 can extend distally from the flanges 272. The flanges 272 can each include an opening 274A and 274B (collectively openings 274) that is configured to receive the pivot pin 282 such that the top jaw 222A can pivot relative the bottom jaw 222B. The flanges 272 (which can be a set of flanges, that is, two flanges) can be rigid or semi-rigid members located at a proximal portion of the top jaw 222A. The flanges 272 of the top jaw 222A can each include a recess 276A and 276B (collectively referred to as recesses 276) that extend into a bottom surface of the flanges 272. For example, flange 272A can include recess 276A and flange 272B can include recess 276B. As discussed herein, these recesses 276 are configured to engage the drive bar 214 via the drive pin 252 coupled to the drive bar strut 242. For example, the drive pin 252 extends through the drive bar strut 242 and into the recesses 276 to couple the top flange 272A to the drive bar 214. Thus, as the drive bar 214 is moved linearly, the linear motion is translated into rotational motion to rotate the top jaw 222A relative the bottom jaw 222B between a closed position and a closed position.

The bottom jaw 2229 can include the bottom jaw 266, the bottom insulating portion 268, and the bottom grip plate 270. The bottom jaw 2229 can include flanges 278A (collectively referred to as the flanges 278). An elongated body 284 can extend distally from the flanges 278. The flanges 278 can each include an opening 280A and 280B (collectively openings 280) that is configured to receive the pivot pin 282 such that the top jaw 222A can pivot relative the bottom jaw 2229. The flanges 278 (which can be a set of flanges, that is, two flanges) can be rigid or semi-rigid members located at a proximal portion of the bottom jaw 222B.

The flanges 278 of the bottom jaw 222B can define an opening 300 along the top of the bottom jaw 222B. As discussed herein, the opening 300 can receive the flanges 272 of the upper jaw 222A such that flanges 272 are positioned laterally inward from the flanges 278. In an example, the bottom jaw 2229 can include projections 292A and 292B (collectively projections 292) extending proximally into the opening 300, as seen in FIG. 15A. The projections 292 in combination with the flanges 278 form slots 293A and 2939 (collectively slots 293) that receive the flanges 272 of the top jaw 222A. The gap 295 between the slots 293 form a portion of the blade channel 281B that can guide the blade 216 into the top and bottom jaws 222A and 222B. The blade channel 2819 can extend along the elongated body 284 of the bottom plate 222B.

In an example, the bottom jaw 2229 can define a shoulder 301. When assembled, a distal end of the outer shaft 212 can abut the shoulder 301 as one or more portions of the bottom jaw 222B extend into or receive a portion of the outer shaft 212 to couple the bottom jaw 222B to the outer shaft 212.

As seen in FIGS. 15B and 15C, the bottom jaw 222B can have an opening 303 along the bottom surface. The opening 303 is configured to allow engagement and movement between the top jaw 222A and the drive bar 214. In an example, a proximal end 294 of the projections 292 can form a stop surface such that the distal translation of the drive bar 214 is limited by the distal end of the drive bar strut 242 contacting the proximal end 294 of the projections 292. However, other configurations, alone or in combination with the proximal end 294, can be used for limiting the distal translation of the drive bar 214.

FIGS. 16A-16D illustrate the drive bar 214. FIG. 16A illustrates a side-view of the drive bar 213, FIG. 16B illustrates a top town view of the drive bar 214, FIG. 16C illustrates a bottom-up view of the drive bar 214, and FIG. 16D illustrates a front-end view or distal view of the drive bar 214.

As discussed herein, the drive bar shaft 240 can include the axial tracks 243 that can receive the guide 50 such that the drive bar 214 can move relative to the guide 50. The distal portion 241 of the drive bar shaft 240 can couple with the drive bar strut 242, as discussed herein.

The drive bar strut 242 extends from a proximal portion to a distal portion 248 and includes a first wall 316A and a second wall 3169 (collectively referred to as walls 316). The walls 316 define a channel 318 and are connected along a bottom surface 239. The channel 318 is configured to receive the blade 216. The drive bar strut 242 includes a drive pin portion 250, at the distal portion 248, that defines an opening 251 that is configured to receive the drive pin 252. As shown in FIG. 16A, the opening 251 does not include a closed perimeter. However, in some examples, the opening 251 has a closed perimeter. The opening 251 is positioned laterally inward from the outer diameter (the periphery) of the drive bar shaft 240. As disused herein, opening 251 can align with the recesses 276 of the top jaw 222A. The drive pin 252 extends across the drive bar strut 242 and at least partially into the recesses 276. As in FIG. 16A, the opening 251 that receives the drive pin 252 is below the longitudinal axis A2.

Between the drive bar shaft 240 and the drive bar strut 242 a shoulder 314 is defined. The shoulder 314 can abut the distal end 279 or the bottom jaw 222B when the jaws 222 are in the open configuration. That is, distal translation of the drive bar 214 can, in some examples, be limited by the shoulder 314 abutting the distal end 279 of the bottom jaw 222B. Further, a distal end 312 of the drive bar strut 242 can abut the proximal end 294 of the projections 292 of the bottom jaw 222B. Thus, distal translation of the drive bar 214 can, in some examples, be limited by the distal end 312 of the drive bar strut 242 contacting the proximal end 294 of the projections 292.

Figure 17B:
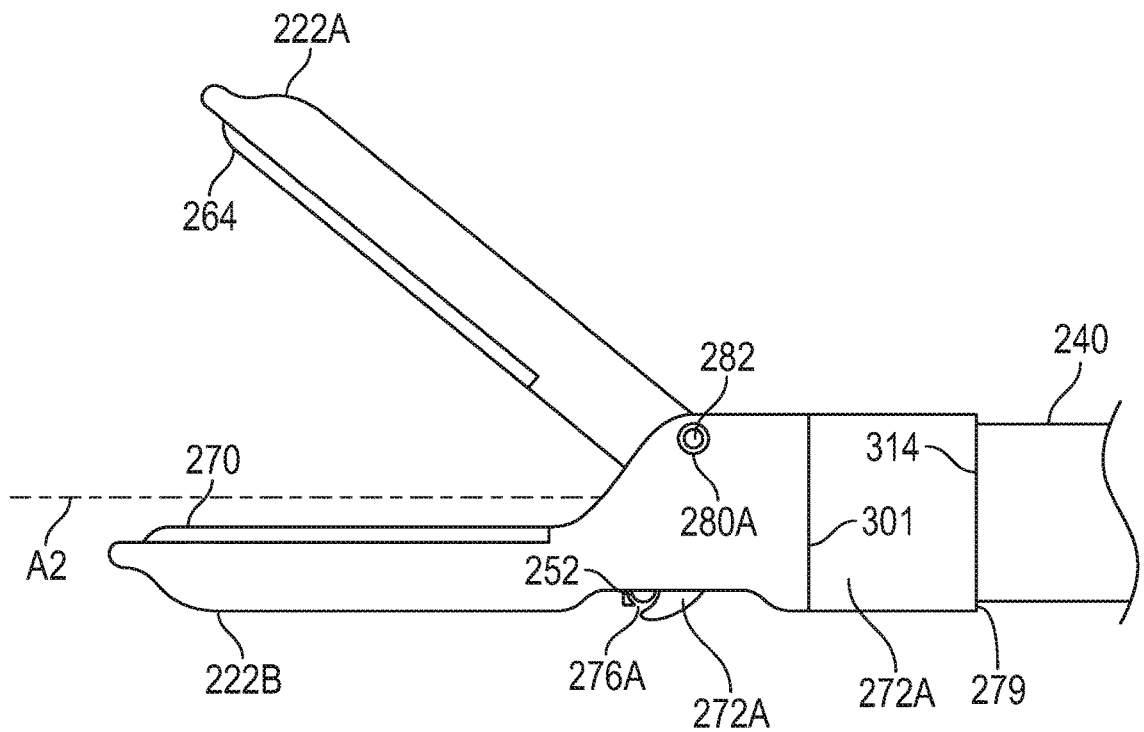
FIG. 17B illustrates a side-view of the end effector of the forceps in FIG. 17A showing the jaws in an open position.
Figure 17C:
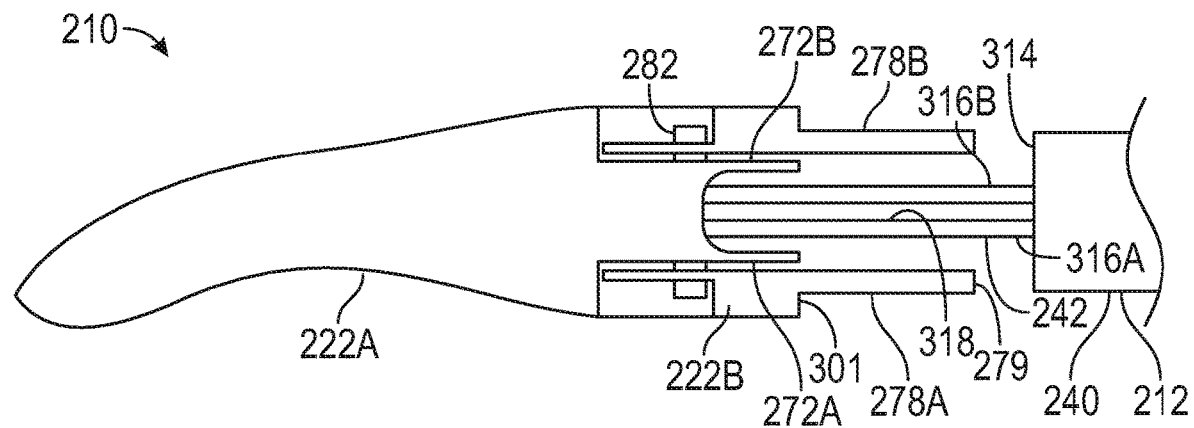
FIG. 17C illustrates a top-down view of the end effector of the forceps in FIG. 17A.
Figure 17D:
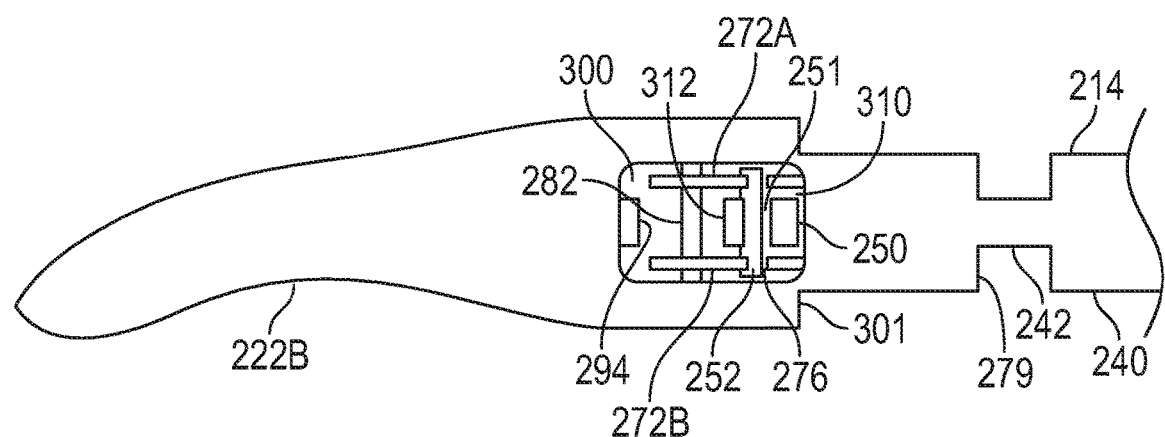
FIG. 17D illustrates a bottom-up view of the end effector of the forceps in FIG. 17A.
Figure 18:
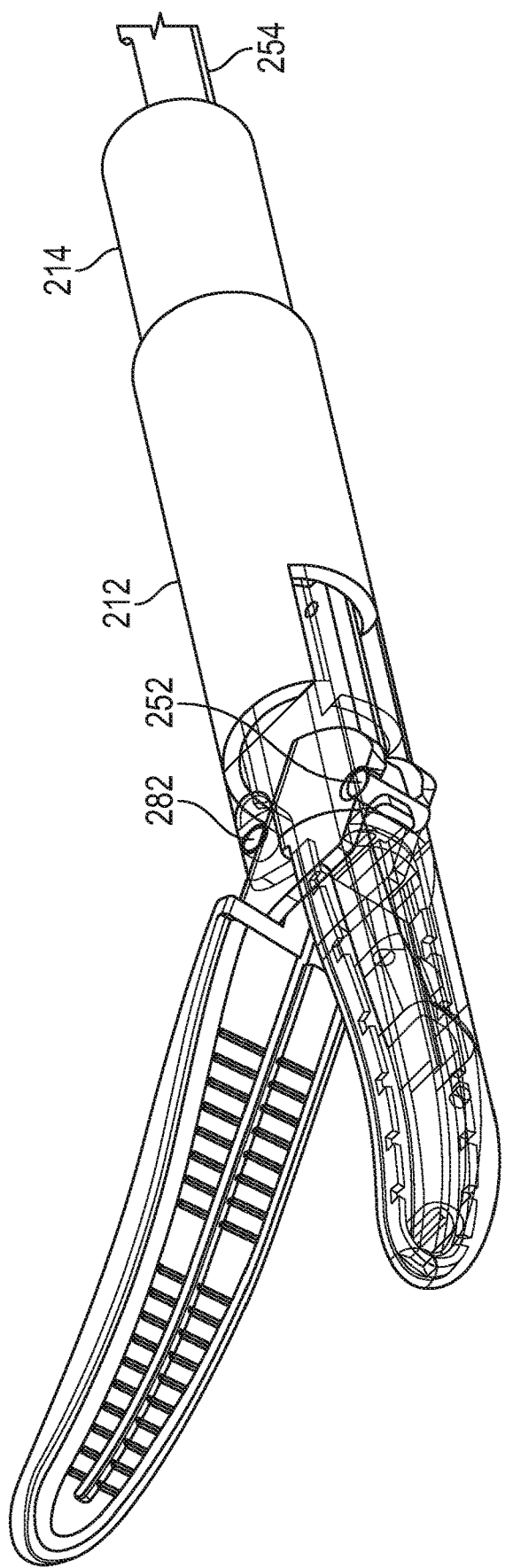
FIG. 18 illustrates a perspective view of the end effector of the forceps showing the jaws in an open position, in accordance with at least one example of this disclosure.

Referring now to FIGS. 17-18 that illustrate an assembled view of a portion of the forceps 210 including the end effector 220. FIG. 17A illustrates a side-view of the end effector 220 of the forceps 210 showing the jaws 222 in a closed position, FIG. 17B illustrates a side-view of the end effector 220 of the forceps 210 in FIG. 17A showing the jaws 222 in an open position, FIG. 17C illustrates a top-down view of the end effector 220 of the forceps in FIG. 17A, FIG. 17D illustrates a bottom-up view of the end effector 220 of the forceps 210 in FIG. 17A, and FIG. 18 illustrates a perspective view of a portion of the forceps 210 with a portion of the jaw body 266 of the bottom jaw 222B being translucent. FIGS. 17A-17D are shown without the outer shaft 212 (FIG. 11) and FIGS. 17B-17D are shown without the blade 216 for simplicity.

As seen in FIG. 17A, the jaws 222 are in a closed position. As discussed herein, the bottom jaw 222B is rigidly coupled to the outer shaft 212 and the top jaw 222B is rotationally coupled to the bottom jaw 222B via the pivot pin 282. In the closed position, a portion of the flanges 272 and a portion of the drive pin portion 250 are partially visible in the opening 303. The recesses 276 and the opening 251 (see FIG. 16A) are aligned and the drive pin 252 is positioned therein. As seen in FIG. 17A, there is a vertical offset V1 between the pivot axis (pivot pin 282) and the line of action of the drive pin 252. The vertical offset V1 between the pivot axis of the pivot pin 282 and the line of action of the drive pin 252 can be such that both are below or above the longitudinal axis or where one is along the longitudinal axis A2 and the other is above or below the longitudinal axis A2. As seen in FIG. 17A, the pivot pin 282 and the drive pin 252 are both offset from the longitudinal axis A2. For example, the drive pin 252 (positioned within opening 251 of drive pin portion 250) is offset below the longitudinal axis A2. Similarly, the pivot pin 282 (positioned through the first and second jaws 222) is offset above the longitudinal axis A2. In this instance, the lever arm can be increased and there is sufficient room for the blade 216 to travel between the pivot pin 282 and the drive pin 252. For example, blade 216 is shown in FIG. 17A as passing between the pivot pin 282 and the drive pin 252 and can be centered about the longitudinal axis A2.

In the closed position, the distal end 279 of the bottom jaw 222B and the shoulder 314 defined between the drive bar shaft 240 and the drive bar strut 242 are spaced apart. When the jaws 222 are in an open position, the shoulder 314 can abut the distal end 279, as seen in FIG. 17B. As seen in FIG. 17B, the drive bar 214 was moved distally and the linear motion translated to rotational motion and rotated the top jaw 222A relative to the bottom jaw 222B. As seen in FIG. 17B, the bottom portion of the flanges 272 can extend slightly beyond the diameter of the outer tube 212. However, the amount that will extend beyond the diameter of the outer tube 212 is minimized and the shape of the bottom portion is such that it can minimize damage to surrounding tissue during use.

To close the jaws 222, proximal linear motion can be applied to the drive bar 214. In doing so, the drive pin portion 250 pulls the drive pin 252 proximally and thereby rotates the top jaw 222A from the open position back to the closed position.

FIG. 17C illustrates a top-down view of the forceps 210. As seen in FIG. 17C, the flanges 272 of the top jaw 222A are positioned laterally inward to the flanges 278 of the bottom jaw 222B. Further, the drive bar strut 242 is positioned laterally inward to the flanges 272, 278. While not shown with the blade 216 (see FIG. 11), the channel 318 defined by the drive bar strut 242 is configured to receive the blade 216 such that the blade can translate along the channel 318 and into the jaws 222.

FIG. 17D illustrates a bottom-up view of the portion of the forceps 210 where the jaws 222 are in a closed position. As seen in FIG. 17D, the drive pin 252 is positioned within the drive pin portion 250 of the drive bar strut 242 and within the recesses of the flanges 272.

While illustrative examples of a medical device are shown and described in this disclosure with respect to a forceps, the features can be used in other medical devices besides forceps for controlling end effectors used in diagnosis, treatment or surgery. Any representation of a forceps or description thereto is shown primarily for illustrative purposes to disclose features of various examples.

The forceps illustrated in the examples can be an electrosurgical device, however, the forceps may be any type of medical device that facilitates mechanical and/or electrical actuation of one or more end effectors or other elements arranged distal from the handpiece having one or more actuation systems. The actuation systems described, which can extend, retract or rotate one or more shafts to produce this result, can be used to effect actions in other medical devices (e.g., medical instruments).

In operation of some examples, a handle (such as those discussed above) can be operated to translate the drive bar 214 within (and with respect to) the outer shaft 212. For example, distal translation of the drive bar 214 with respect to the outer shaft 212 can cause the jaws 222 to move from a closed position (as shown in FIG. 17A) to an open position (as shown in FIGS. 10,17B, and 18). Conversely, proximal translation of the drive bar 214 can cause the jaws 222 to move from an open position to the closed position, such that the translation of the drive bar 214 can translate the top jaw 222A to rotate relative to the bottom jaw 222B.

More specifically, in one example, distal translation of the drive bar 214 can cause the drive pin 252 to translate distally while coupled to the drive bar 214 and the top jaw 222A. Because the drive pin 252 is coupled to the drive bar 214 and the top jaw 222A and the top jaw 222A is coupled to the pivot pin 282, the, distal translation of the drive shaft 214 causes the top jaw 222A to open and rotate about the pivot pin 282. That is, the top jaw 222A opens or rotates about the pivot pin 252 and relative to the bottom jaw 12B toward (an ultimately into) an open position.

Distal translation of the drive bar 214 can be limited by contact between the distal end the drive bar 214 and a proximal end 294 of projections 292 of the bottom jaw 222B. In some examples, distal translation of the drive bar 214 can be limited by contact between the guide 238 and a proximal end of the axial tracks 243. In some example, the distal translation of the drive bar 214 can be limited by contact between distal end 279 of the bottom jaw 2229 and a shoulder 314 defined between the drive bar shaft 240 and the drive bar strut 242.

To close the jaws, the drive bar 214 can be translated proximally, which causes the drive pin 252 to translate proximally. As the drive pin 252 translates proximally, the top jaw 222A rotates about the pivot pin 282 from the open position toward (an ultimately into) a closed position). Proximal translation of the drive shaft 214 can be limited by contact between the guide 50 and a distal end of each of the axial tracks 243. In other examples, proximal translation of the inner shaft 26 can be limited by contact between the top jaw 222A and the bottom jaw 222B.

VARIOUS EXAMPLES & NOTES

Each of these non-limiting examples can stand on its own, or can be combined in various permutations or combinations with one or more of the other examples.

Example 1 provides a surgical forceps, comprising: an outer shaft extending from a proximal portion to a distal portion and defining a longitudinal axis; an inner shaft located within the outer shaft and extending along the longitudinal axis, the inner shaft including a projection at the distal portion of the inner shaft; a first jaw rigidly coupled to the distal portion of the outer shaft; and a second jaw pivotably moveable relative to the first jaw, the second jaw including a set of flanges located at a proximal portion of the second jaw, each flange of the set of flanges engagable with the projection of the inner tube, the inner shaft translatable within the outer shaft to pivot the second jaw relative to the first jaw and the outer shaft between open and closed positions.

In Example 2, the subject matter of Example 1 can optionally include a pivot pin securable to the second jaw, wherein the pivot pin is vertically offset from the projection.

In Example 3, the subject matter of Example 2 can optionally include where the pivot pin is positioned along the longitudinal axis.

In Example 4, the subject matter of Examples 1-3 can optionally include where the inner shaft includes: a pair of axial tracks located on opposite sides of the inner shaft, the pair of axial tracks arranged to receive a guide therein, the guide secured to the outer shaft, wherein the inner shaft is movable relative to the guide as the inner shaft translates relative to the outer shaft and wherein proximal portions of the respective axial tracks are engageable with the guide to limit distal translation of the inner shaft relative to the outer shaft.

In Example 5, the subject matter of Examples 1-4 can optionally include a blade located within the inner tube and extending axially through the first jaw and the second jaw in a position laterally inward of the set of flanges of the first jaw.

In Example 6, the subject matter of Examples 1-5 can optionally include where the projection includes at least one set of openings.

In Example 7, the subject matter of Example 6 can optionally include where each flange of the set of flanges includes at least one tooth configured to engage with a respective opening of the at least one set of openings of the projection of the inner shaft.

In Example 8, the subject matter of Example 7 can optionally include where the first jaw includes a body portion having a first tooth receiving opening and a second tooth receiving opening, the first and second tooth receiving openings positioned along a bottom side of the body portion opposite an opening along a top side of the body portion.

In Example 9, the subject matter of Examples 1-8 can optionally include where the first and second tooth receiving openings are separated by a strut of the body portion, wherein the at least one set of openings of the projection of the inner shaft are lateral openings such that a first opening of the at least one set of openings is aligned within the first tooth receiving opening and a second opening of the at east one set of openings is aligned with the second tooth receiving opening.

Example 10 provides a surgical forceps comprising: an outer shaft extending from a proximal portion to a distal portion and defining a longitudinal axis; a drive bar located within the outer tube and extending along the longitudinal axis, the drive bar including: a drive bar shaft extending from a proximal portion to a distal portion; and a drive bar strut coupled to the distal portion of the drive bar shaft; a first jaw rigidly coupled to the distal portion of the outer shaft, the first jaw including a first set of flanges; and a second jaw pivotably moveable relative to the first jaw, the second jaw including a second set of flanges located at a proximal portion of the second jaw, each flange of the second set of flanges coupled to the drive bar strut of the drive bar, the drive bar translatable within the outer shaft to pivot the second jaw relative to the first jaw and the outer shaft between open and closed positions.

In Example 11, the subject matter of claim 10 can optionally include a pivot pin securable to the second set of flanges.

In Example 12, the subject matter of Example 11 can optionally include where the pivot pin is offset from the longitudinal axis.

In Example 13, the subject matter of Examples 10-12 can optionally include a drive pin securable to the drive bar strut and the second set of flanges.

In Example 14, the subject matter of Example 13 can optionally include where the drive pin is offset from the longitudinal axis.

In Example 15, the subject matter of Examples 10-14 can optionally include a blade located within the drive bar and extending along the longitudinal axis, the blade translatable to extend between the drive bar strut, the first jaw, and the second jaw.

In Example 16, the subject matter of Example 15 can optionally include wherein the second set of flanges are located laterally inward from the first set of flanges.

In Example 17, the subject matter of Example 16 can optionally include where the drive bar strut is located laterally inward from the second set of flanges.

Example 18 provides a surgical forceps, comprising: an outer shaft extending from a proximal portion to a distal portion and defining a longitudinal axis; a drive bar located within the outer shaft and extending along the longitudinal axis, the drive bar including: a drive bar shaft extending from a proximal portion to a distal portion; and a drive bar strut coupled to the distal portion of the drive bar shaft; a first jaw rigidly coupled to the distal portion of the outer tube, the first jaw having a first set of flanges located at a proximal portion of the first jaw; a second jaw pivotably moveable relative to the first jaw and the outer tube, the second jaw including a second set of flanges located at a proximal portion of the second jaw; a pivot pin securable to the second set of flanges, wherein the pivot pin is offset from the longitudinal axis; and a drive pin securable to the drive bar strut and the second set of flanges, wherein the drive pin is offset from the longitudinal axis, the drive bar translatable within the outer shaft to drive the drive pin in a first direction along the outer shaft to pivot the second jaw, about the pivot pin, between a closed position and an open position.

In Example 19, the subject matter of Example 18 can optionally include where the pivot pin is offset above the longitudinal axis and the drive pin is offset below the longitudinal axis.

In Example 20, the subject matter of Example 19 can optionally include a blade located within the drive bar and extending axially between the pivot pin and the drive pin and into the first jaw and the second jaw.

Example 21 is any one or combination of the Examples or elements of the Examples 1-20.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." in this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A surgical forceps, comprising:
   an elongate outer shaft including a proximal portion and a distal portion and defining a central longitudinal axis extending along a center of a bore of the outer shaft;
   an inner shaft located within the outer shaft and extending along the central longitudinal axis, the inner shaft including a projection at a distal portion of the inner shaft;
   a first jaw rigidly coupled to the distal portion of the outer shaft; and
   a second jaw pivotably connected to at least one of the outer shaft or the first jaw about a pivot point, the pivot point being intersected by a plane orthogonal to the central longitudinal axis and the pivot point located at a distal portion of the outer shaft, wherein the pivot point is laterally offset, in a direction away from the first jaw, from the intersection of the plane and the central longitudinal axis, the second jaw including a set of flanges located at a proximal portion of the second jaw, each flange of the set of flanges engageable with the projection of the inner shaft, the inner shaft proximally retractably translatable within the outer shaft to pivot the second jaw toward the first jaw and toward a closed position.

2. The surgical forceps of claim 1, wherein the inner shaft includes:
   a pair of axial tracks located on opposite sides of the inner shaft, the pair of axial tracks arranged to receive a guide therein, the guide secured to the outer shaft, wherein the inner shaft is movable relative to the guide as the inner shaft translates relative to the outer shaft and wherein proximal portions of the respective axial tracks are engageable with the guide to limit distal translation of the inner shaft relative to the outer shaft.

3. The surgical forceps of claim 1, further including:
   a blade located within the inner shaft and extending axially through the first jaw and the second jaw in a position laterally inward of a set of flanges of the first jaw.

4. The surgical forceps of claim 1, wherein:
   an engagement between (1) the projection at the distal portion of the inner shaft and (2) the second jaw is located on the flanges at a location that is further from the distal end of the second jaw than the pivot point.

5. A surgical forceps, comprising:
   an elongate outer shaft including a proximal portion and a distal portion and defining a longitudinal axis;
   an inner shaft located within the outer shaft and extending along the longitudinal axis, the inner shaft including a projection at the distal portion of the inner shaft;
   a first jaw rigidly coupled to the distal portion of the outer shaft;
   a second jaw pivotably moveable relative to the first jaw, the second jaw including a set of flanges located at a proximal portion of the second jaw, each flange of the set of flanges engagable with the projection of the inner shaft, the inner shaft translatable within the outer shaft to pivot the second jaw relative to the first jaw and the outer shaft between open and closed positions; and a drive pin attached to the inner shaft and securable to the projection at the distal portion of the inner shaft and the set of flanges;

wherein the projection includes at least one set of openings;

wherein each flange of the set of flanges includes at least one tooth configured to engage with a respective opening of the at least one set of openings of the projection of the inner shaft.

6. The surgical forceps of claim 5, wherein the first jaw includes a body portion having a first tooth receiving opening and a second tooth receiving opening, the first and second tooth receiving openings positioned along a bottom side of the body portion opposite an opening along a top side of the body portion.

7. The surgical forceps of claim 6, wherein the first and second tooth receiving openings are separated by a strut of the body portion, wherein the at least one set of openings of the projection of the inner shaft are lateral openings such that a first opening of the at least one set of openings is aligned within the first tooth receiving opening and a second opening of the at least one set of openings is aligned with the second tooth receiving opening.

8. A surgical forceps, comprising:
an elongate outer shaft including a proximal portion and a distal portion and defining a longitudinal axis
a drive bar located within the outer shaft and extending along the longitudinal axis, the drive bar including:
a drive bar shaft extending from a proximal portion to a distal portion; and
a drive bar strut coupled to the distal portion of the drive bar shaft;
a first jaw rigidly coupled to the distal portion of the outer shaft, the first jaw including a first set of flanges; and
a second jaw pivotably moveable relative to the first jaw, the second jaw including a second set of flanges located at a proximal portion of the second jaw, each flange of the second set of flanges coupled to the drive bar strut of the drive bar, the drive bar translatable within the outer shaft to pivot the second jaw relative to the first jaw and the outer shaft between open and closed positions;
wherein:
a projection of the drive bar shaft includes at least one set of openings;
an individual flange of the second set of flanges includes at least one tooth configured to engage with a respective opening of the at least one set of openings of the projection of the drive bar shaft; and
the first jaw includes a body portion having a first tooth receiving opening and a second tooth receiving opening, the first and second tooth receiving openings positioned along a bottom side of the body portion opposite an opening along a top side of the body portion.

9. The surgical forceps of claim 8, further including:
a pivot pin securable to the second set of flanges.

10. The surgical forceps of claim 9, wherein the pivot pin is offset from the longitudinal axis.

11. The surgical forceps of claim 8, wherein the drive pin is offset from the longitudinal axis.

12. The surgical forceps of claim 8, further including:
a blade located within the drive bar and extending along the longitudinal axis, the blade translatable to extend between the drive bar strut, the first jaw, and the second jaw.

13. The surgical forceps of claim 12, wherein the second set of flanges are located laterally inward from the first set of flanges.

14. The surgical forceps of claim 13, wherein the drive bar strut is located laterally inward from the second set of flanges.

15. A surgical forceps, comprising:
an elongate outer shaft including a proximal portion and a distal portion and defining a longitudinal axis;
a drive bar located within the outer shaft and extending along the longitudinal axis, the drive bar including:
a drive bar shaft extending from a proximal portion to a distal portion; and
a drive bar strut coupled to the distal portion of the drive bar shaft;
a first jaw rigidly coupled to the distal portion of the outer shaft, the first jaw having a first set of flanges located at a proximal portion of the first jaw;
a second jaw pivotably moveable relative to the first jaw and the outer shaft, the second jaw including a second set of flanges located at a proximal portion of the second jaw;
a pivot pin securable to the second set of flanges, wherein the pivot pin is offset from the longitudinal axis in a direction away from the first jaw; and
a drive pin securable to the drive bar strut and the second set of flanges, wherein the drive pin is offset from the longitudinal axis, the drive bar translatable within the outer shaft to drive the drive pin in a proximal direction along the outer shaft to pivot the second jaw, about the pivot pin, toward a closed position.

16. The surgical forceps of claim 15, wherein the pivot pin is offset above the longitudinal axis and the drive pin is offset below the longitudinal axis.

17. The surgical forceps of claim 16, further including:
a blade located within the drive bar and extending axially between the pivot pin and the drive pin and into the first jaw and the second jaw.

18. A surgical forceps, comprising:
an outer shaft defining a central longitudinal axis;
an inner reciprocating shaft configured to translate at least partially through the outer shaft along the central longitudinal axis;
a first jaw connected to the outer shaft;
a second jaw pivotably connected to at least one of the outer shaft or the first jaw about a pivot point, the second jaw including at least two linkage teeth; and
a planar blade extending and translatable along the central longitudinal axis and arranged within and encompassed by the inner reciprocating shaft;
wherein:
the second jaw engages the inner reciprocating shaft at the at least two linkage teeth to define a linkage encompassed by at least one of the outer shaft or the first jaw, the at least two linkage teeth of the linkage configured to receive longitudinal force from the inner reciprocating shaft translated along the longitudinal axis, wherein the at least two linkage teeth include a proximal tooth and a distal tooth arranged closer to a distal end of the forceps than the proximal tooth when the first and second jaws are in a closed position; and the linkage translates the longitudinal force received by the at least two linkage teeth of the linkage to rotate the second jaw about the pivot point towards the first jaw.

19. The surgical forceps of claim 18, wherein:

the at least two linkage teeth are separated by a concavity therebetween, the concavity sized and shaped to receive a detent connected to the inner reciprocating shaft; and the concavity is configured to translate the longitudinal force in both proximal and distal directions to rotate the second jaw about the pivot point toward or away from the first jaw.

20. The surgical forceps of claim 18, wherein:

the pivot is intersected by a plane, wherein the plane is:
established orthogonal to the longitudinal axis; and
located at a distal end of the outer shaft; and
the pivot is laterally offset from the intersection of the plane and the longitudinal axis.

21. The surgical forceps of claim 18, wherein the inner reciprocating shaft includes a series of cavities, the cavities defining a toothed rack and sized and shaped to engage a pinion feature defined by the at least two linkage teeth of the second jaw at the linkage.

22. The surgical forceps of claim 21, wherein the at least two teeth of the second jaw, defining the pinion feature, include a series of teeth arranged radially with respect to the pivot point, the pinion feature configured to engage with a respective cavity of the series of cavities of the inner reciprocating shaft.

23. The surgical forceps of claim 18, wherein the first jaw includes at least one extension opening sized and shaped to allow a proximal portion of the second jaw to protrude therethrough as the linkage translates the longitudinal force to rotate the second jaw about the pivot point away from the first jaw.

* * * * *